United States Patent
Otvos et al.

(10) Patent No.: US 11,124,837 B2
(45) Date of Patent: Sep. 21, 2021

(54) METHODS AND SYSTEMS FOR PREDICTING COLORECTAL CANCER INCIDENCE AND MORTALITY

(71) Applicant: LipoScience, Inc., Raleigh, NC (US)

(72) Inventors: James D. Otvos, Cary, NC (US); Sarnia Mora, Cambridge, MA (US); Paulette Denise Chandler, Walpole, MA (US)

( * ) Notice: Subject to any disclaimer, the term of this patent is extended or adjusted under 35 U.S.C. 154(b) by 542 days.

(21) Appl. No.: 15/612,719

(22) Filed: Jun. 2, 2017

(65) Prior Publication Data

US 2018/0112274 A1   Apr. 26, 2018

Related U.S. Application Data

(60) Provisional application No. 62/345,453, filed on Jun. 3, 2016.

(51) Int. Cl.
| | |
|---|---|
| *G01R 33/20* | (2006.01) |
| *G01N 33/68* | (2006.01) |
| *G16B 25/00* | (2019.01) |
| *G01R 33/465* | (2006.01) |
| *G01N 33/574* | (2006.01) |
| *G16B 25/10* | (2019.01) |
| *C12Q 1/6886* | (2018.01) |
| *G16B 99/00* | (2019.01) |

(52) U.S. Cl.
CPC ..... *C12Q 1/6886* (2013.01); *G01N 33/57407* (2013.01); *G01N 33/57419* (2013.01); *G01N 33/57488* (2013.01); *G01R 33/20* (2013.01); *G01R 33/465* (2013.01); *G16B 25/00* (2019.02); *G16B 25/10* (2019.02); *C12Q 2600/118* (2013.01); *G01N 33/68* (2013.01); *G01N 2800/50* (2013.01); *G16B 99/00* (2019.02)

(58) Field of Classification Search
CPC ............ C12Q 1/6886; C12Q 2600/118; G01N 33/57407; G01N 33/57419; G01N 33/57488; G01N 33/68; G01N 2800/50; G01R 33/20; G01R 33/465; G16B 25/00; G16B 25/10; G16B 99/00

See application file for complete search history.

(56) References Cited

PUBLICATIONS

Otvos et al. (Clinical Chemistry, 2015, 61(5):714-723) (Year: 2015).*
Doyle et al. (CA Cancer J, 2006, 56:323-353) (Year: 2006).*
Scott et al. (European Journal of Oncology Nursing, 2005, 9:131-137) (Year: 2005).*

* cited by examiner

*Primary Examiner* — Jeremy C Flinders

(74) *Attorney, Agent, or Firm* — Kilpatrick Townsend & Stockton LLP

(57) ABSTRACT

Disclosed are methods and systems that uses GlycA concentration in biosamples to evaluate risks of CRC incidence and mortality.

17 Claims, 12 Drawing Sheets

METHODS AND SYSTEMS FOR PREDICTING COLORECTAL CANCER INCIDENCE AND MORTALITY

CROSS-REFERENCES TO RELATED APPLICATIONS

This application claims the benefit of and priority to U.S. Provisional Application Ser. No. 62/345,453, filed on Jun. 3, 2106, the contents of which are hereby incorporated by reference as if recited in full herein.

FIELD OF INVENTION

The present invention relates generally to analysis of in vitro biosamples. The invention may be particularly suitable for NMR analysis of human blood plasma and serum.

BACKGROUND

Colorectal cancer ("CRC") is the second leading cause of cancer-related deaths in the United States and it causes about 50,000 deaths each year. The risk factors for CRC include advanced age (the risk for CRC significantly increases after age 50), smoking, a diet high in fat, and the lack of physical activity.

Currently, carcinoembryonic antigen (CEA) is considered the crucial biomarker for monitoring CRC recurrence and prognosis. However, using CEA to identify incident CRC in clinical applications has serious limitations due to CEA's low specificity for CRC. Duffy et al., Clinical Chemistry. April 2001; 47(4):624-630. Studies that aimed at searching for inflammatory biomarkers that could be used to predict the risk of having CRC have not been able to establish any consistent associations between inflammatory biomarkers and incident colorectal cancer. Erlinger et al. JAMA. Feb. 4 2004; 291(5): 585-590; Zhang et al., Ann. Intern. Med. Mar. 15 2005; 142 (6): 425-432. For example, the investigation of the relationship between the circulating high-sensitivity C-reactive protein (hsCRP) concentrations and CRC risk produced inconsistent results. Thus, the need for a biomarker that can be used to accurately predict or assess the risk of developing colorectal cancer and/or mortality remains great.

SUMMARY OF THE INVENTION

Described herein are methods for determining the risk of CRC incidence or mortality using a novel systemic inflammatory biomarker of protein glycan N-acetyl groups (GlycA). The present invention may be embodied in a variety of ways.

In one aspect, the invention provides methods for determining the risk of CRC incidence or mortality for a subject, the methods comprising: providing a sample comprising a biological sample from the subject; measuring the GlycA concentration, and determining the risk of developing CRC based on the GlycA concentration. In various embodiments, the risk may be CRC incidence or mortality in the next 5-20 years. For example, the risk may be CRC incidence or mortality in the next 5, 6, 7, 8, 9, 10, 11, 12, 13, 14, 15, 16, 17, 18, 19, or 20 years. In one embodiment, the method determines the risk of CRC incidence or mortality in the next 9 years, or 12 years, or 15 years, or 18 years, or 19 years, or 20 years. In one embodiment, the subject is a healthy subject. In one embodiment, the subject is one having CRC and the method determines the risk of mortality for the subject.

In one embodiment, the method determines the subject as having increased risk of CRC incidence or mortality when the GlycA concentration is in the third or fourth quartile, or a third tertile of a population norm. In one embodiment, the method determines the subject as having increased risk of CRC incidence or mortality when the GlycA concentration is at least about 370 µmol/L (third quartile). Or, the method may determine the subject as having increased risk of CRC incidence or mortality when the GlycA concentration is at least about 400 µmol/L (third tertile) Or, the method may determine the subject as having increased risk of CRC incidence or mortality when the GlycA concentration is greater than about 415 µmol/L (fourth quartile), Thus, in certain embodiments the risk for having CRC incidence or mortality may be evaluated as low (≤350 µmol/L), intermediate (in the range of about 350-400 µmol/L), or high (≥400 µmol/L).

In another aspect, the methods for determining the risk of CRC incidence or mortality for a subject comprise providing a sample from a subject, measuring the concentration of GlycA and at least one acute phase protein and/or at least one inflammatory protein and/or at least one lipoprotein. The at least one acute phase protein may be hsCRP, fibrinogen, or sICAM-1. In some embodiments, the determining the risk of CRC incidence or mortality is based on a CRC risk index comprising the GlycA concentration and the concentration of the at least one acute phase protein and/or at least one inflammatory protein and/or at least one lipoprotein. In certain embodiments, the at least one or more acute phase proteins comprises at least one of sICAM-1, hsCRP or fibrinogen. In one embodiment, the at least one lipoprotein comprises Apo A1.

In yet another aspect, the invention provides a method to determine the risk of developing a CRC tumor at a higher Duke stage, a tumor having a proximal location, or a tumor being less differentiated. The method comprises
(a) providing a sample from the subject,
(b) measuring the GlycA concentration, and
(c) determining the subject has an increased risk of developing a CRC tumor at a higher Duke stage, having a proximal location, or being less differentiated for at least one of when the GlycA concentration in the sample is in the third or fourth quartile, or the third tertile of a population norm. For example, the method may determine the subject as having increased risk of CRC incidence or mortality when the GlycA concentration is at least about 370 µmol/L (third quartile). Or, the method may determine the subject as having increased risk of CRC incidence or mortality when the GlycA concentration is at least about 400 µmol/L (third tertile). Or, the method may determine the subject as having increased risk of CRC incidence or mortality when the GlycA concentration greater than about 415 µmol/L (fourth quartile). Thus, in certain embodiments the risk for having CRC incidence or mortality may be evaluated as low (≤350 µmol/L), intermediate (in the range of about 350-400 µmol/L), or high (≥400 µmol/L).

In yet another aspect, the invention provides a method of evaluating whether a treatment is effective in reducing chance of CRC incidence or mortality for the subject, comprising obtaining samples from the subject for at least two time points during the treatment period, measuring the GlycA concentration in the samples using a NMR spectrometer, and determining the therapy is ineffective if the GlycA concentration increases over time, or determining the therapy is effective if the GlycA concentration does not increase over time.

In yet another aspect, the invention provides a computer program product for evaluating the risk of CRC incidence or mortality for a subject. The computer program product may comprise computer readable program code for obtaining NMR signal data of a sample of a subject to determine the GlycA concentration in the sample, and computer readable program code for electronically identifying the subject has increased risk of CRC incidence or mortality for at least one of when the GlycA concentration in the sample is within the third or fourth quartile, or the third tertile of a population norm. For example, the method may determine the subject as having increased risk of CRC incidence or mortality when the GlycA concentration is at least about 370 µmol/L (third quartile). Or, the method may determine the subject as having increased risk of CRC incidence or mortality when the GlycA concentration is at least about 400 µmol/L (third tertile). Or, the method may determine the subject as having increased risk of CRC incidence or mortality when the GlycA concentration greater than about 415 µmol/L (fourth quartile). Thus, in certain embodiments the risk for having CRC incidence or mortality may be evaluated as low (≤350 µmol/L), intermediate (in the range of about 350-400 µmol/L), or high (≥400 µmol/L). In one embodiment, the computer program product for determining the risk of CRC incidence or morality is based on a CRC risk index comprising the concentration of GlycA and the concentration of at least one acute phase protein and/or at least one inflammatory protein and/or at least one lipoprotein. In certain embodiments, the at least one or more acute phase proteins comprises at least one of sICAM-1, hsCRP or fibrinogen. In one embodiment, the at least one lipoprotein comprises Apo A1.

In yet another aspect, the invention provides a computer program product for evaluating whether a treatment is effective in reducing the risk of CRC incidence or mortality for the subject. The computer program product may comprise computer readable program code that obtains NMR signal data of samples taken at two or more time points during the treatment period, computer readable program code for determining the GlycA concentration in the samples, and computer readable program code for determining the treatment is ineffective if the GlycA concentration increases over time, and determining the treatment is effective if the GlycA concentration does not increase over time, e.g., if the Glyc A concentration decreases over time. The method may comprise generating a patient report comprising the GlycA concentration that indicates whether the subject has increased risk of CRC incidence or mortality. In certain embodiments, the report may further comprise a risk value that is based on the concentration of an acute phase protein and/or at least one inflammatory protein and/or at least one lipoprotein. For example, the acute phase protein may comprise one of fibrinogen, hsCRP or sICAM-1. In one embodiment, the at least one lipoprotein comprises Apo A1.

In yet another aspect, the invention provides a system for determining the risk of CRC incidence or mortality for a subject. The system may comprise an NMR spectrometer for acquiring at least one NMR spectrum of a sample, and a controller in communication with the NMR spectrometer. The controller may comprise at least one processor configured to (i) determine the GlycA concentration from the sample based on the NMR signal data, and (ii) determine the subject has increased risk of CRC incidence or mortality for at least one of when the GlycA concentration is in third or fourth quartile, or third tertile of the population norm. For example, the system may determine the subject as having increased risk of CRC incidence or mortality when the GlycA concentration is at least about 370 µmol/L (third quartile). Or, the system may determine the subject as having increased risk of CRC incidence or mortality when the GlycA concentration is at least about 400 µmol/L (third tertile) Or, the system may determine the subject as having increased risk of CRC incidence or mortality when the GlycA concentration greater than about 415 µmol/L (fourth quartile), Thus, in certain embodiments the risk for having CRC incidence or mortality may be evaluated as low (≤350 µmol/L), intermediate (in the range of about 350-400 µmol/L), or high (≥400 µmol/L).

In various embodiments of the methods, computer products and systems, the risk may be CRC incidence or mortality in the next 5-20 years. For example, the risk may be CRC incidence or mortality in the next 5, 6, 7, 8, 9, 10, 11, 12, 13, 14, 15, 16, 17, 18, 19, or 20 years. When measuring GlycA concentration is an embodiment of any aspect of the invention, the measuring step is preferably performed using a NMR spectrometer.

Further aspects of the invention are described in detail below.

BRIEF DESCRIPTION OF THE DRAWINGS

The present application includes the following figures. The figures are intended to illustrate certain embodiments and/or features of the invention, and to supplement any description(s) of the invention. The figures do not limit the scope of the invention, unless the written description expressly indicates that such is the case.

DETAILED DESCRIPTION

Figure 1A:
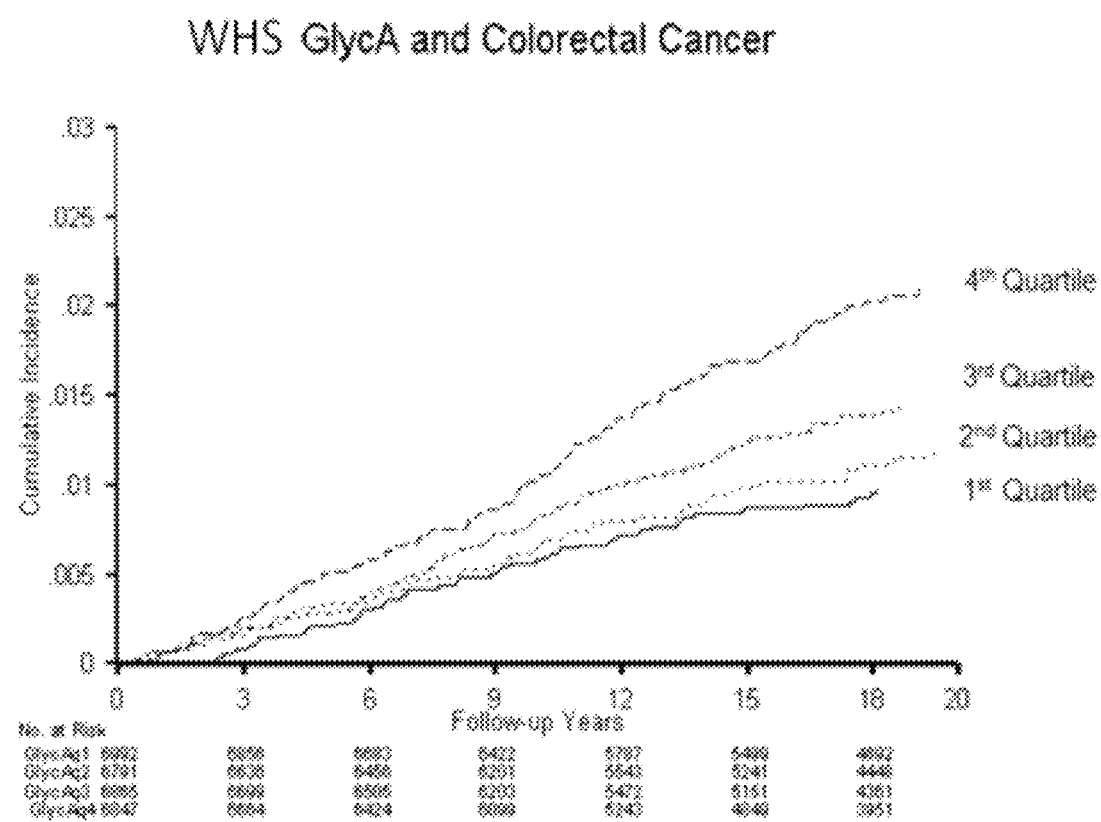
FIG. 1A and FIG. 1B show the colorectal cancer cumulative incidence according to GlycA quartile in the Women's Healthy Study ("WHS") (FIG. 1A) and GlycA Tertiles Multi-Ethnic Study of Atherosclerosis ("MESA") (FIG. 1B).

The following description recites various aspects and embodiments of the present invention. No particular embodiment is intended to define the scope of the invention. Rather, the embodiments merely provide non-limiting examples various methods and systems that are at least included within the scope of the invention. The description is to be read from the perspective of one of ordinary skill in the art; therefore, information well known to the skilled artisan is not necessarily included.

1. Definitions

The following terms, unless otherwise indicated, shall be understood to have the following meanings:

As used herein, the terms "a," "an," and "the" can refer to one or more unless specifically noted otherwise.

Throughout this application, the term "about" is used to indicate that a value includes the inherent variation of error for the device, the method being employed to determine the value, or the variation that exists among the study subjects.

As used herein, the term "biomarker" is any biomolecule that may provide biological information about the physiological state of an organism. In certain embodiments, the presence or absence of the biomarker may be informative. In other embodiments, the concentration of the biomarker may be informative. A biomarker may be a neurotransmitter, such as serotonin, or a metabolite of a neurotransmitter.

As used herein, the terms "subject," "individual," and "patient" are used interchangeably. The use of these terms does not imply any kind of relationship to a medical professional, such as a physician.

As used herein, the term "biological sample" is used to refer to any fluid or tissue that can be isolated from an individual. For example, a biological sample may be whole blood, plasma, serum, other blood fraction, urine, cerebrospinal fluid, tissue homogenate, saliva, amniotic fluid, bile, mucus, peritoneal fluid, lymphatic fluid, perspiration, tissues, tissue homogenate, and the like. Embodiments of the invention may be particularly suitable for evaluating human blood plasma or serum biosamples, particularly for GlycA.

As used herein, the term "GlycA" refers to a biomarker that is derived from a measure of composite NMR signal from carbohydrate portions of acute phase reactant glycoproteins containing N-acetylglucosamine and/or N-acetylgalactosamine moieties, more particularly from the protons of the 2-NAcGlc and 2-NAcGal methyl groups. The GlycA signal is centered at about 2.00 ppm in a plasma NMR spectrum at about 47° C. The peak location is independent of spectrometer field but may vary depending on analysis temperature of the biosample. Thus, the GlycA peak region may vary if the temperature of the test sample varies. The GlycA NMR signal may include a subset of NMR signal at the defined peak region so as to include only clinically relevant signal contributions and may exclude a protein contribution to the signal in this region as will be discussed further below.

As used herein, the terms "population norm" and "standard" refer to values defined by a large study or studies such as the Women's Health Study (WHS) or the Multi-Ethnic Study of Atherosclerosis (MESA) or other study having a large enough sample to be representative of the general population. However, the instant invention is not limited to the population values in WHS or MESA as the presently defined normal and at-risk population values or concentrations may change over time. Thus, a reference range associated with values from a defined population can be provided and used to assess elevated or reduced concentrations and/or risk of CRC incidence or mortality.

As used herein, the term "NMR spectral analysis" means using proton ($^1$H) nuclear magnetic resonance spectroscopy techniques to obtain data that can measure the respective parameters present in the biosample, e.g., blood plasma or blood serum. "Measuring" and derivatives thereof refers to determining a concentration or concentration and/or for certain lipoprotein subclasses, measuring the average particle size thereof. The term "NMR derived" means that the associated measurement is calculated using NMR signal/spectra from one or more scans of an in vitro biosample in an NMR spectrometer.

As used herein, the terms "mathematical model" and "model" are used interchangeably and when used with "CRI", "CRC risk index", or "risk" refer to a statistical model of risk used to evaluate a subject's risk of CRC incidence or mortality in the future, typically within 5-20 years. The risk model can be or include any suitable model including, but not limited to, one or more of a logistic model, a mixed model or a hierarchical linear model. The risk model can provide a measure of risk based on the probability of CRC incidence or mortality within a defined time frame, typically within 5-20 years.

As used herein, the term "risk of CRC incidence" refers to the likelihood of a subject developing colorectal cancer, e.g., showing one or more of the symptoms commonly associated with colorectal cancer or showing positive result in one or more of the screening tests prescribed by a medical professional. The common symptoms of CRC include not are not limited to, a change in bowel habits, such as diarrhea, constipation, or narrowing of the stool, that lasts for more than a few days, rectal bleeding, blood in the stool, cramping or abdominal (belly) pain, weakness and fatigue, unintended weight loss.

As used herein, the term "risk of CRC mortality", or "risk of mortality" refers to the likelihood of a subject will die due to the presence of a colorectal cancer.

As used herein, the term "CRC risk factor" refers to the factors, that the value of which being too high or too low may increase a person's chance of developing CRC. Non-limiting CRC risk factors include age, aspirin or Nonsteroidal anti-inflammatory drug ("NSAID") use, race, family history of CRC, alcohol, lack of exercise, smoking, menopausal status, postmenopausal hormone use (never, past, current), healthy eating index (Alternative Healthy Eating Index, "AHEI"), which is based on foods and nutrients predictive of chronic disease risk), multivitamin use, intake of red meat (servings/day), total vegetable and fruits (servings/day), supplemental and dietary calcium, fiber (grams/day), total calories (kcal/day); history of colonic polyps, body mass index (BMI), and hemoglobin A1C. Some of these risk factors can be avoided, and some cannot.

As used herein, the term "risk-factor adjusted model" refers to a multivariable model for determining the risk of having CRC that is compensated for the effect caused by known CRC risk factors, so that samples from subjects having different GlycA concentrations can be compared with confidence. Several risk-factor adjusted models are used in this disclosure. "WHS-model 1" refers to a model, used in WHS study, that is adjusted for trial treatment assignments and age. "WHS-model 2" refers to a model, also used in WHS study, that is adjusted for trial treatment assignments, age, race, family history of CRC, alcohol, exercise, smoking, menopausal status, postmenopausal hormone use (never, past, current), healthy eating index (Alternative Healthy Eating Index, "AHEI"), which is based on foods and nutrients predictive of chronic disease risk), multivitamin use, intake of red meat (servings/day), total vegetable and fruits (servings/day), supplemental and dietary calcium, fiber (grams/day), total calories (kcal/day); history of colonic polyps, body mass index (BMI), and hemoglobin A1C. MESA-model 1 refers to a model that is adjusted for age, sex, and race/ethnicity. MESA-model 2 is a model that is adjusted for age, sex, and race/ethnicity, BMI, exercise (total intentional exercise MET-hrs/wk), smoking, alcohol (drinks/week), and family history of cancer. A third risk-factor adjusted model, model 3, adjusts for all the CRC risk factors in model 2, in either WHS-model 2 or MESA-model 2, plus one of the acute phase proteins, hsCRP, fibrinogen, or sICAM-1.

As used herein, the term "person-years" refers to a measurement combining the number of persons and their time contribution in a study and is the sum of individual units of time that the persons in the study population have been exposed to or are at risk for the conditions of interest. For purposes of this disclosure, person-years is the summation, for all subjects in the study, of the time each was monitored for the development of CRC or CRC death.

2. Measuring the GlycA Concentration in a Sample a. Samples

These methods disclosed herein include providing a sample comprising a biological sample. In this context, the term "providing" is to be construed broadly. The term is not intended to refer exclusively to a subject who provided a biological sample. For example, a technician in an off-site clinical laboratory can be said to "provide" the sample, for example, as the sample is prepared for purification by chromatography.

The sample is preferably an in vitro biosample, but is not limited to any particular sample type. The biological sample may also include other components, such as solvents, buffers, anticlotting agents, and the like. In some embodiments, the biological sample can be one or more of whole blood, plasma, serum, urine, cerebrospinal fluid, tissue homogenate, saliva, amniotic fluid, bile, mucus, peritoneal fluid, or lymphatic fluid. In some embodiments, the biological sample is obtained from a drug-treated subject. For example, the biological sample can be obtained from a subject treated with an anti-CRC therapy. The invention is not limited to any particular volume of biological sample. In some embodiments, the biological sample is at least about 1-100 µL, at least about 10-75 µL, or at least about 15-50 µL in volume. In certain embodiments, the biological sample is at least about 20 µL in volume.

In preferred embodiments, the biological sample is a blood, plasma, or serum sample. In a particular embodiment of the invention, the biological sample is a blood sample. Blood samples are typically collected in EDTA tubes and stored prior to analysis in vapor-phase liquid nitrogen (−170° C. for WHS) or low-temperature freezer (−70° C. for MESA).

b. Measuring GlycA

In preferred embodiments, the GlycA concentration in a sample is determined based on a composite NMR signal from carbohydrate portions of acute phase reactant glycoproteins containing N-acetylglucosamine and/or N-acetylgalactosamine moieties. The GlycA signal is centered at about 2.00 ppm in a plasma NMR spectrum at about 47° C. The peak location is independent of spectrometer field but may vary depending on analysis temperature of the biosample. Thus, the GlycA peak region may vary if the temperature of the test sample varies. The GlycA NMR signal may include a subset of NMR signal at the defined peak region so as to include only clinically relevant signal contributions and may exclude a protein contribution to the signal in this region as will be discussed further below. The composite NMR signal can be deconvolved to quantify the signal contributions of GlycA using any of the defined mathematical deconvolution models that are recognized by one of ordinary skill in the art. Methods of how to determine GlycA based on the NMR signals are well known, for example, as described in the published US patent application US 2013-0328561-A1, the entirety of the disclosure is herein incorporated by reference. In preferred embodiments, the GlycA concentration in a sample is determined by measuring the subset of mobile N-acetylglucosamine (GlcNAc) residues on the bi-, tri-, and tetra-antennary glycan branches of circulating glycoproteins in a patient plasma sample (FIG. 4), through deconvolving the GlycA signal from 400 Hz $^1$H NMR spectrum at 2.00 ppm.

While NMR measurements of GlycA concentrations are contemplated as being particularly suitable for the analyses described herein, other technologies may be used to measure these parameters now or in the future and embodiments of the invention are not limited to the NMR measurement methodology.

3. Measuring the Concentrations of Other Acute Phase Proteins, hsCRP, Fibrinogen, and sICAM Inflammation is known to play a role in tumorigenesis. See Klampfer et al. Curr. Cancer Drug Targets (2011) 11(4): 451-464. Acute phase proteins, also known as acute phase reactants, are a class of proteins whose plasma concentrations increase or decrease in response to inflammation. Acute phase proteins are typically produced by liver in response to cytokines produced by local inflammatory cells when injury occurs. They are relevant to many key biological processes including cell adhesion, molecular trafficking and clearance, signal transduction, modulation of the innate immune system and inflammation. A high concentration of acute phase protein hsCRP in the blood may be a sign that there may be an inflammatory process occurring in the body, which can indicate a host of other health concerns, including infection, arthritis, kidney failure, and pancreatitis. In some cases, a greater than 3.0 mg/L of hsCRP indicates a high risk for developing heart disease.

Tests for hsCRP concentrations can be performed on blood samples and can be administered with a cholesterol screening or other routine blood work. hsCRP is typically measured using immunometric assays, and commercial kits are available from e.g., Denka Seiken (Tokyo, Japan), Cat #hsCRP-Latex (II) X2 "Seiken"; Thermo Fisher (California, Calif.), Cat #KHA0031; and Cayman Chemical (Michigan, USA), Cat #10011236.

Soluble intracellular adhesion molecule 1 (sICAM-1) is present in low concentrations in the membranes of leukocytes and endothelial cells and has also been implicated in playing a role in signal transduction in proinflammatory pathways. sICAM-1 is typically measured using an enzyme-linked immunosorbent assay. Commercial kits for measuring sICAM-1 are readily available, for example, from R&D Systems, Minneapolis, Minn.

Fibrinogen is a plasma protein essential for blood clot formation and can be transformed by thrombin into a fibrin gel (the "clot"). Fibrinogen is an acute phase reactant, and an increase in fibrinogen level may indicate a number of acquired conditions. For example, acute or chronic inflammatory illnesses, nephrotic syndrome, liver disease and cirrhosis, pregnancy or estrogen therapy, compensated intravascular coagulation, can result in an increase in its plasma concentration. Healthy males typically have a fibrinogen concentration of 200-375 mg/dL and healthy females of 200-430 mg/dL.

Fibrinogen concentration in a patient can be determined by a variety of ways. For example, it can be assessed using a fibrinogen activity test, which measures the function of fibrinogen and its ability to be converted into fibrin. The Clauss clotting method can be used to assess the function of fibrinogen and its ability to be converted into fibrin. The method is based on the principle that in the presence of an excess of thrombin, the clotting time of diluted plasma is inversely proportional to the concentration of plasma fibrinogen. The clot can be detected by an instrument that detects viscosity, e.g., the STA-R Evolution from Diagnostica Stago, Inc. Parsippany, N.J. The amount of fibrinogen can also be assessed using an immunoturbidimetric assays, commercially available from e.g., Kamiya Biomedical, Seattle, Wash.

4. Determining the Risk of CRC Incidence or Mortality for a Subject a. Determining the Risk of CRC Incidence or Mortality Using GlycA Concentration Incident colorectal cancer and mortality and the GlycA concentration are analyzed using the multivariable Cox proportional hazards models, which are adjusted for one or more of the CRC risk factors ("risk-factor adjusted models"). The CRC risk factors include, but are not limited to, treatment assignments, age, race, family history of CRC, alcohol, exercise level, smoking, menopausal status, post-menopausal hormone use (never, past, current), healthy eating index (Alternative Healthy Eating Index, "AHEI"), which is based on foods and nutrients predictive of chronic disease risk), multivitamin use, intake of red meat (servings/day), total vegetable and fruits (servings/day), supplemental and dietary calcium, fiber (grams/day), total calories (kcal/day); history of colonic polyps, body mass index (BMI), and hemoglobin A1C, and markers of systemic inflammation (natural log transformed [ln]hsCRP, fibrinogen, or sICAM-1). Non-limiting examples of the risk-factor adjusted model include WHS-model 1, WHS-model 2, MESA-model 1, and MESA-model 2. Thus, in some cases, the risk of CRC incidence or mortality is determined using a mathematical model that includes the GlycA concentration, wherein the model is adjusted for one or more clinical variables selected from the group consisting of trial treatment assignments and age. In some cases, the risk of CRC incidence or mortality is determined using a mathematical model that includes the GlycA concentration, wherein the model is adjusted for one or more clinical variables selected from the group consisting of trial treatment assignments, age, race, family history of CRC, alcohol, exercise, smoking, menopausal status, post-menopausal hormone use (never, past, current), healthy eating index (Alternative Healthy Eating Index, "AHEI"), multivitamin use, intake of red meat (servings/day), total vegetable and fruits (servings/day), supplemental and dietary calcium, fiber (grams/day), total calories (kcal/day); history of colonic polyps, body mass index (BMI), and hemoglobin A1C.

A High GlycA Concentration is Associated with Increased CRC Incidence and Mortality To determine the risk of CRC incidence or mortality, GlycA concentrations of a population norm is obtained by measuring the GlycA concentration in samples from subjects in a reference population, for example, patient population in WHS or MESA. The data are stratified by quantiles, e.g., by quartiles or tertiles. The value ranges for each quantile may vary among different population norms, but it is within the skill of a person of ordinary art to choose a reference population and to determine the GlycA concentration ranges for each quantile of the population norm. In some cases, the reference population used to determine the GlycA concentrations associated with a population norm include the entire population in a database. In some case, the reference population include only subjects who have certain common specific characteristics, e.g., being female. In some embodiments, the selected reference population include at least 500, 1,000, 2,000, 3,000, 4,000, 5,000, 6,000, 8,000, 10,000, 15,000, 20,000, 40,000, 60,000, 80,000, or 100,000 different individuals. For example, using the entire WHS participants as a reference population, the GlycA concentration range was less than 326 µmol/L in the first quartile, 327-369 µmol/L in the second quartile, 370-416 µmol/L in the third quartile, and greater than 416 µmol/L in the fourth quartile of the population norm.

A GlycA concentration in upper quartiles, i.e., third, fourth quartiles, is associated with a higher value of CRC risk factors, such as BMI and smoking (Table 1) and also Higher concentrations of acute phase proteins hsCRP, sICAM-1, and fibrinogen.

Figure 1B:
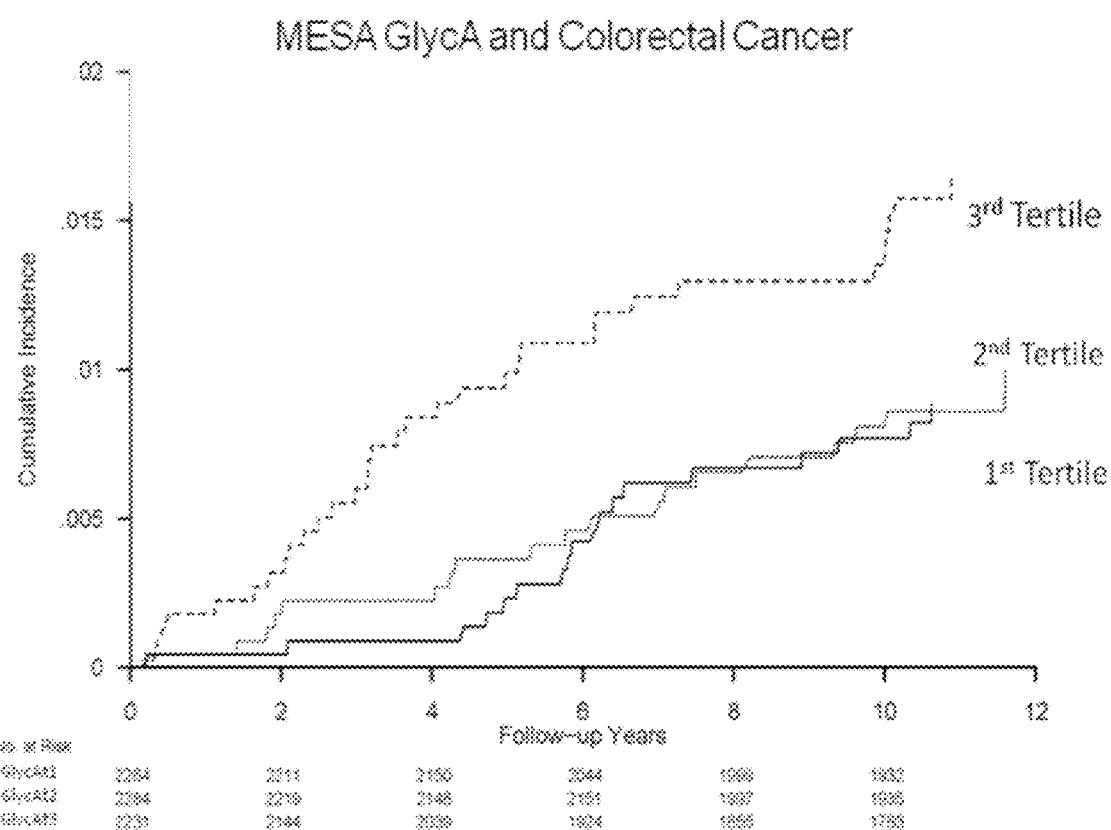

For example, in certain embodiments, increasing quartiles of GlycA are associated with higher numbers of cumulative CRC incidences and mortality, as shown from data in Table 2. In WHS, the CRC incidence rate per 1,000 person-years increased progressively from 0.52, to 1.09 as quartile increases from 1 to 4; CRC death rate per 1,000 person-years showed a similar pattern, increasing from 0.15 to 0.31. Cumulative incidence curves for CRC events (adjusted for age), over a medium of 19 years in WHS and 11 years in MESA, also showed that a higher quartile or tertile of GlycA was associated with a higher cumulative CRC incidence. FIG. 1A and FIG. 1B.

Figure 2A:
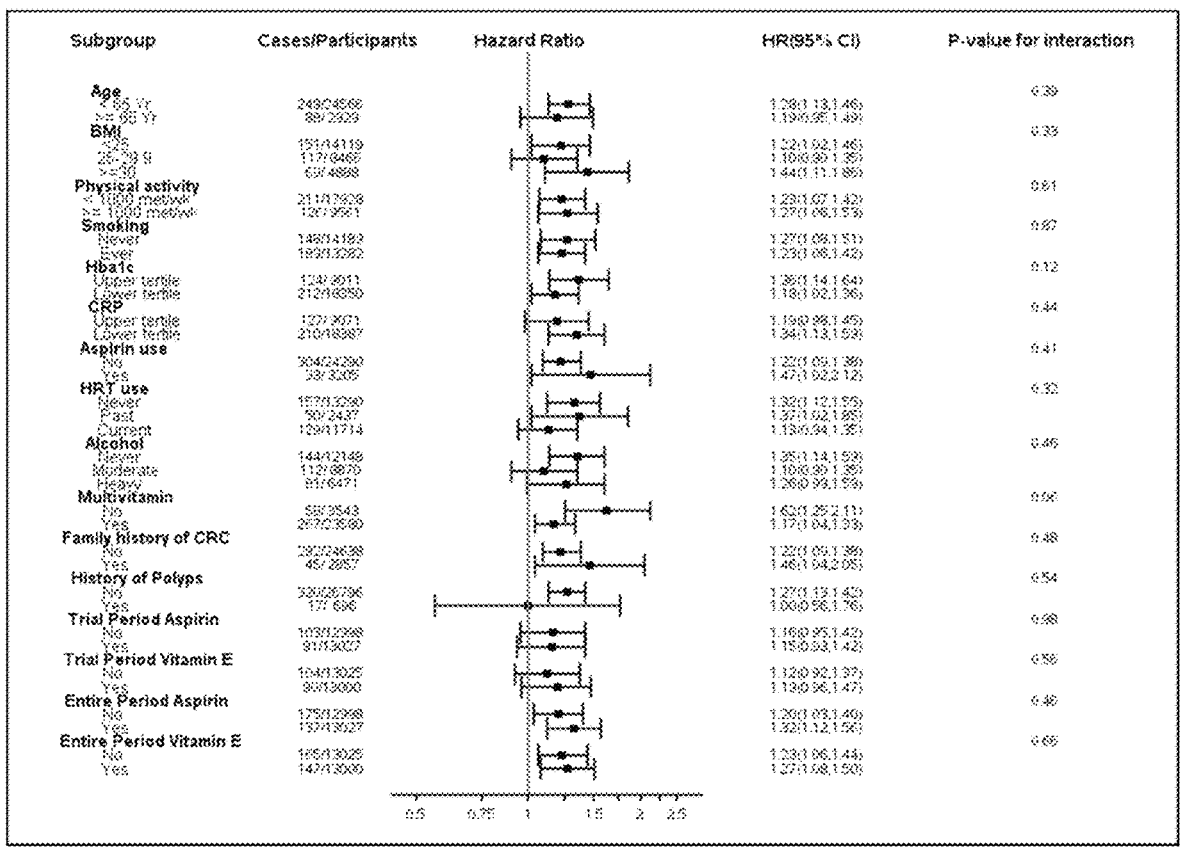
FIGS. 2A and 2B show the hazard ratios ("HR") [95% confidence intervals] per GlycA SD for incident colorectal cancer in various population subgroups (FIG. 2A) and colorectal tumor characteristics (FIG. 2B).

The association between the increasing quartiles of GlycA and higher cumulative CRC incidence is also demonstrated by hazard ratio analysis using risk-factor adjusted models. WHS-model 1 analysis showed that the hazard ratio ("HR") [95% CI] per SD increment of GlycA for CRC incidence was 1.26 [1.13-1.39], $p<0.0001$, and for CRC mortality was 1.29, $p=0.008$. WHS-model 2 analysis showed a hazard ratio [95% CI] of 1.19 (for CRC incidence), $p=0.004$, and 1.24 (for CRC mortality) $p=0.05$. Table 2. The hazard ratios produced from these two models are close in value, indicating adjusting for additional CRC risk factors—those present in WHS-model 2 but not in WHS-model 1—does not appreciably weaken the association between GlycA and CRC incidence/mortality. FIG. 2A also shows when stratified by CRC risk factors such as age, BMI, aspirin or nonsteroidal anti-inflammatory drug ("NSAID") use, increasing GlycA remained associated with increased risk of incident CRC.

Meta-analysis, which combines data from both the WHS and MESA cohorts, also showed that higher CRC incidence (FIGS. 3A and 3B) and mortality (FIGS. 3C and 3D) is associated with higher GlycA quartiles. Both model 1 analysis (FIGS. 3A and 3C) and model 2 analysis (FIGS. 3B and 3D) showed similar results. These data confirmed that a patient's GlycA concentration can be used to determine whether the patient has increased risk of CRC incidence or mortality in a future time frame, e.g., typically in the next 5 to 20 years, using a GlycA concentration in upper quantiles, e.g., third or fourth quartile or third tertile as indicator of a patient having an increased risk of developing CRC and/or dying from CRC.

GlycA is Associated with Risk of CRC Beyond the Acute Phase Proteins

The established systemic inflammatory biomarkers such as hsCRP and sICAM-1 showed no significant associations with CRC incidence or mortality. Another inflammatory biomarker, fibrinogen, was shown to associate with increased risk of CRC death; Quartile 1-Quartile 4 hazard ratios [95% CI] were 1.0 (ref), 0.97 [0.4502.11], 1.79 [0.90-3.57], and 1.81 [0.90-3.66], p for trend=0.04. However, the hazard ratio per SD of fibrinogen increment was not statistically significant, p=0.33. See eTable 2.

In contrast, GlycA's association with the risk of developing CRC and mortality is significant and such association is beyond these known inflammation markers of systemic inflammation. eTable 3 (shown in Example 5, below) shows that the association between incident CRC risk and GlycA remained significant after adjusting for any of the three systemic inflammatory biomarkers (hsCRP, fibrinogen, or sICAM-1). For example, the GlycA risk for CRC incidence and mortality remained significant after incrementally adjusting for hsCRP: HR [95% CI] was 1.27 [1.10-1.45] for CRC incidence and 1.31 [1.01-1.68] for mortality. In models that included both fibrinogen and GlycA, the association between GlycA and CRC became slightly stronger for incident CRC after adjusting for fibrinogen: HR [95% CI] per 1 SD GlycA increased from 1.19 [1.06-1.35] (p=0.004) to 1.22 (p=0.03). The addition of fibrinogen to model 2 had minimal impact on the association between GlycA and CRC death.

GlycA is Associated with Certain Colorectal Tumor Characteristics

Figure 2B:
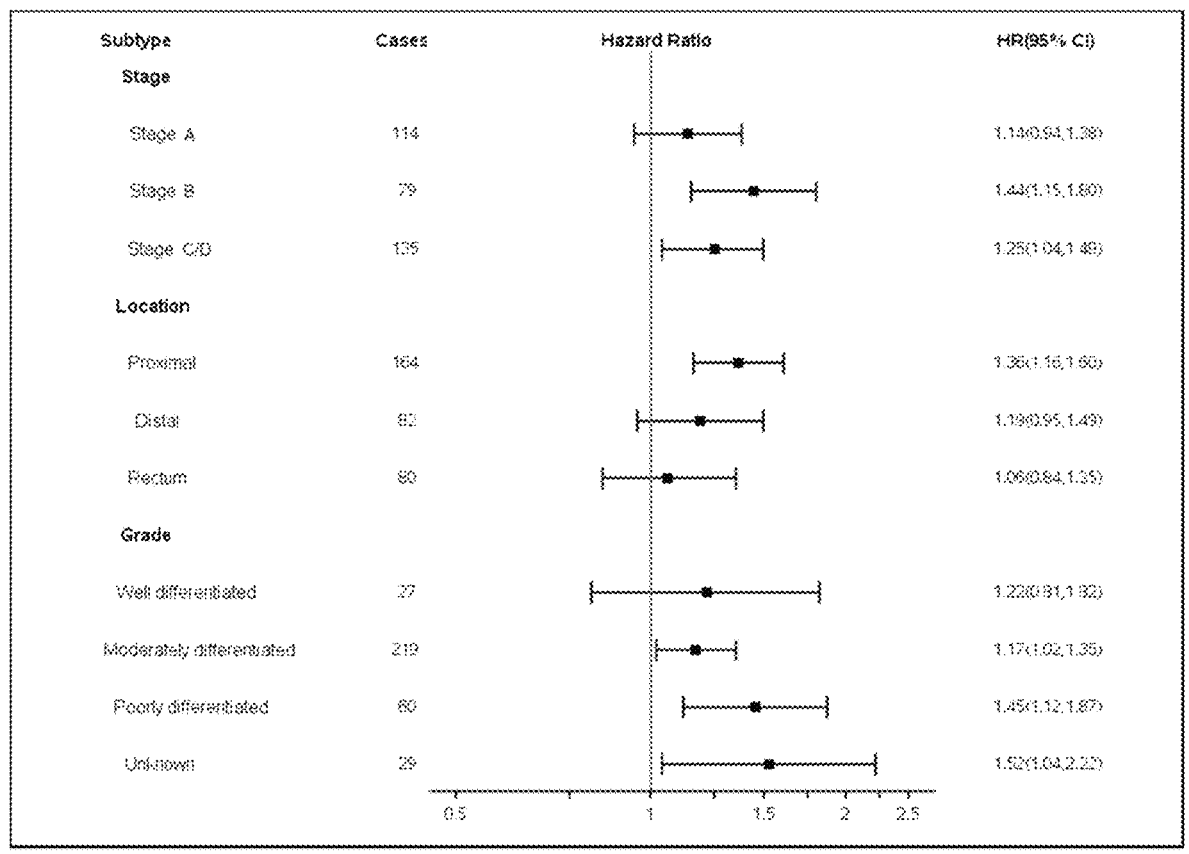

The GlycA concentration in the patient sample can also be used to determine the risk of having certain types of CRCs, e.g., a CRC at a higher Duke stage, a CRC having proximal location, and/or a CRC being less differentiated. Colorectal cancer is commonly classified as Duke Stages A-D. Duke Stage A is when a tumor has invaded into but not through the bowel wall; Duke Stage B is when a tumor has invaded through the bowel wall penetrating the muscle layer but not involving lymph nodes; Duke Stage C is when a tumor involving lymph nodes forms; Duke Stage D is when the tumor becomes metastasized. A higher Duke stage number indicates a more severe form of CRC. The WHS-model 2 analysis in the WHS cohort shows that a higher GlycA level was associated with higher Duke stages, e.g., Stages B, C, and D. Higher GlycA level was also correlated with CRCs having proximal tumor location and being less differentiated. FIG. 2B. Less differentiated tumors tend to spread faster than well differentiated tumors and patients having proximal tumor location generally have significantly worse survival outcomes than those who do not have proximal tumor location. Wong et al. J. Gen. Intern. Med. (2010) 11: 1157-63.

b. Determining the Risk of CRC Incidence or Mortality Using a CRC Index Comprising the GlycA Concentration.

In some cases, as discussed above, the subject's GlycA concentration is directly compared with a population norm to predict the risk of CRC incidence or mortality; for example, a concentration that is in the third or fourth quartile indicate an increased risk for CRC incidence or mortality. In some cases, the GlycA concentration is first converted into a CRC risk index ("CRI"), and the CRI is compared with the CRI range of the population norm. A CRI that is in the third or fourth quartile indicates an increased risk of CRC incidence or mortality.

In some cases, the CRI comprises GlycA concentration and one or more factors that may relate to the development of CRC, for example, the acute phase proteins such as fibrinogen, $\alpha$2-macroglobulin, sICAM-1, and hsCRP. In some cases, the CRI is generated from a multi-parameter equation that includes GlycA concentration and the concentration of the one or more factors known to be related to the development of CRC.

The CRI can be provided as a result expressed numerically or alphanumerically, typically comprising a numerical score on a defined scale or within a defined range of values. For example, in particular embodiments, the risk index can be provided as or include a score within a defined range, such as, for example, between 0-0.1, 0-1, 0-10, 0-24, 0-100, or 0-1000 and the like. Typically, the lowest number is associated with the least risk and the higher numbers are associated with increased risk of CRC incidence or mortality in the future, typically within 9-20 years although over time frames may be used for some embodiments. The lower value in the range may be above "0" such as 1, 2, 3, 4 or 5 and the like, or may even be a negative number (e.g., −1, −2, −3, 4, −5 and the like). Other index examples, include, for example, alphanumeric indexes or even icons noting degrees of risk, including but not limited to, "CRI 1" (low risk), "CRI 5" (intermediate risk) and "CRI 9" (high risk), terms such as "CRI positive", "CRI high", "CRI neutral", "CRI low", "CRI good", "CRI bad", "CRI watch" and the like.

In some case, CRI is presented as a simple guide or predictor of a person's risk status. The "low" value can be associated with the index values that are in the lower half of a population norm. High risk index values can be associated with index values in a fourth quartile or a third tertile of a population norm and indicates a high likelihood of CRC incidence or mortality within the next 5-20 years. Intermediate risk index values can be associated with values in a top half of a population norm but below high risk values.

5. Generating Reports

This invention also provides methods of generating a report useful for determining for a subject the risk of CRC incidence or mortality, the methods comprising: (a) providing a sample from the subject; (b) measuring the GlycA concentration in the sample; (c) determining the risk of CRC incidence or mortality based on the GlycA concentration; and (d) generating a report that recites whether the subject has increased risk of CRC incidence or mortality.

The features and embodiments of all steps except step (d) are described immediately above. The method further includes generating a report that recites the concentration of GlycA in the sample.

6. Computer Program and Systems

Figure 6:
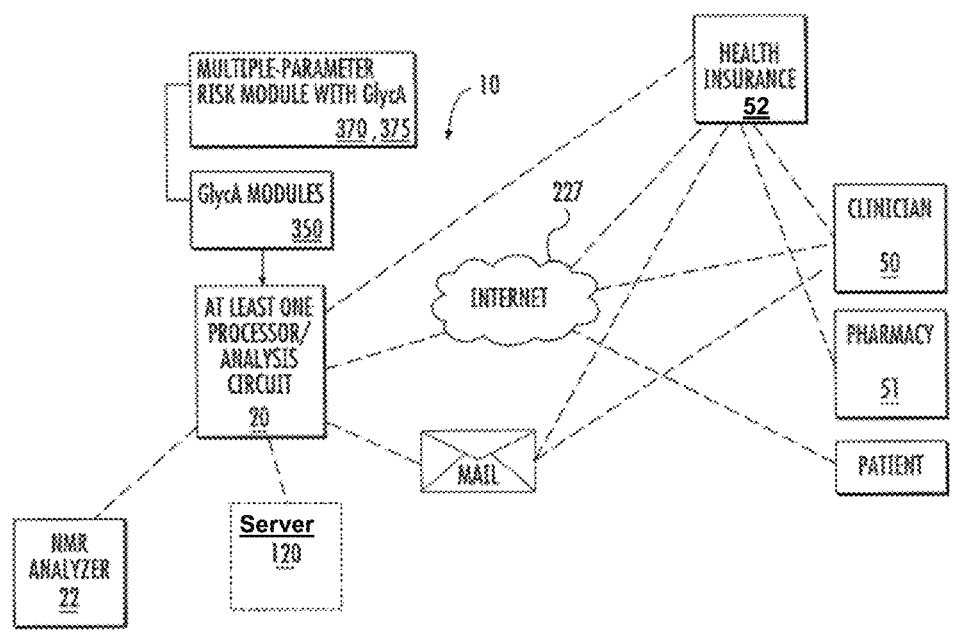
FIG. 6 is a schematic illustration of a system for analyzing the risk of CRC incidence and mortality including a GlycA evaluation module and/or circuit.

The GlycA measurement analysis can be carried out using a system 10 with an NMR clinical analyzer 22 as described in FIG. 6, for example, with respect to FIG. 7 below and/or in U.S. Pat. No. 8,013,602, the contents of which are hereby incorporated by reference as if recited in full herein. The analyzer 22 includes a spectrometer 22s as shown in FIG. 7 and sample handler system.

The system 10 can include a GlycA analysis module and/or circuit 20 that can be onboard the analyzer 22 or at least partially remote from the analyzer 22. If the latter, the analysis module or circuit 20 can reside totally or partially on a server 120. The server 120 can be provided using cloud computing which includes the provision of computational resources on demand via a computer network. The resources can be embodied as various infrastructure services (e.g. computer, storage, etc.) as well as applications, databases, file services, email, etc. In the traditional model of computing, both data and software are typically fully contained on the user's computer; in cloud computing, the user's computer may contain little software or data (perhaps an operating system and/or web browser), and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers. Data transfer can be encrypted and can be done via the Internet using any appropriate firewalls to comply with industry or regulatory standards such as HIPAA. The term "HIPAA" refers to the United States laws defined by the Health Insurance Portability and Accountability Act. The patient data can include an accession number or identifier, gender, age and test data.

The results of the analysis can be transmitted via a computer network, such as the Internet, via email or the like to a patient, clinician site 50, to a health insurance agency 52 or a pharmacy 51. The results can be sent directly from the analysis site or may be sent indirectly. The results may be printed out and sent via conventional mail. This information can also be transmitted to pharmacies and/or medical insurance companies, or even patients that monitor for prescriptions or drug use that may result in an increased risk of an adverse event or to place a medical alert to prevent prescription of a contradicted pharmaceutical agent. The results can be sent to a patient via email to a "home" computer or to a pervasive computing device such as a smart phone or notepad and the like. The results can be as an email attachment of the overall report or as a text message alert, for example.

Figure 7:
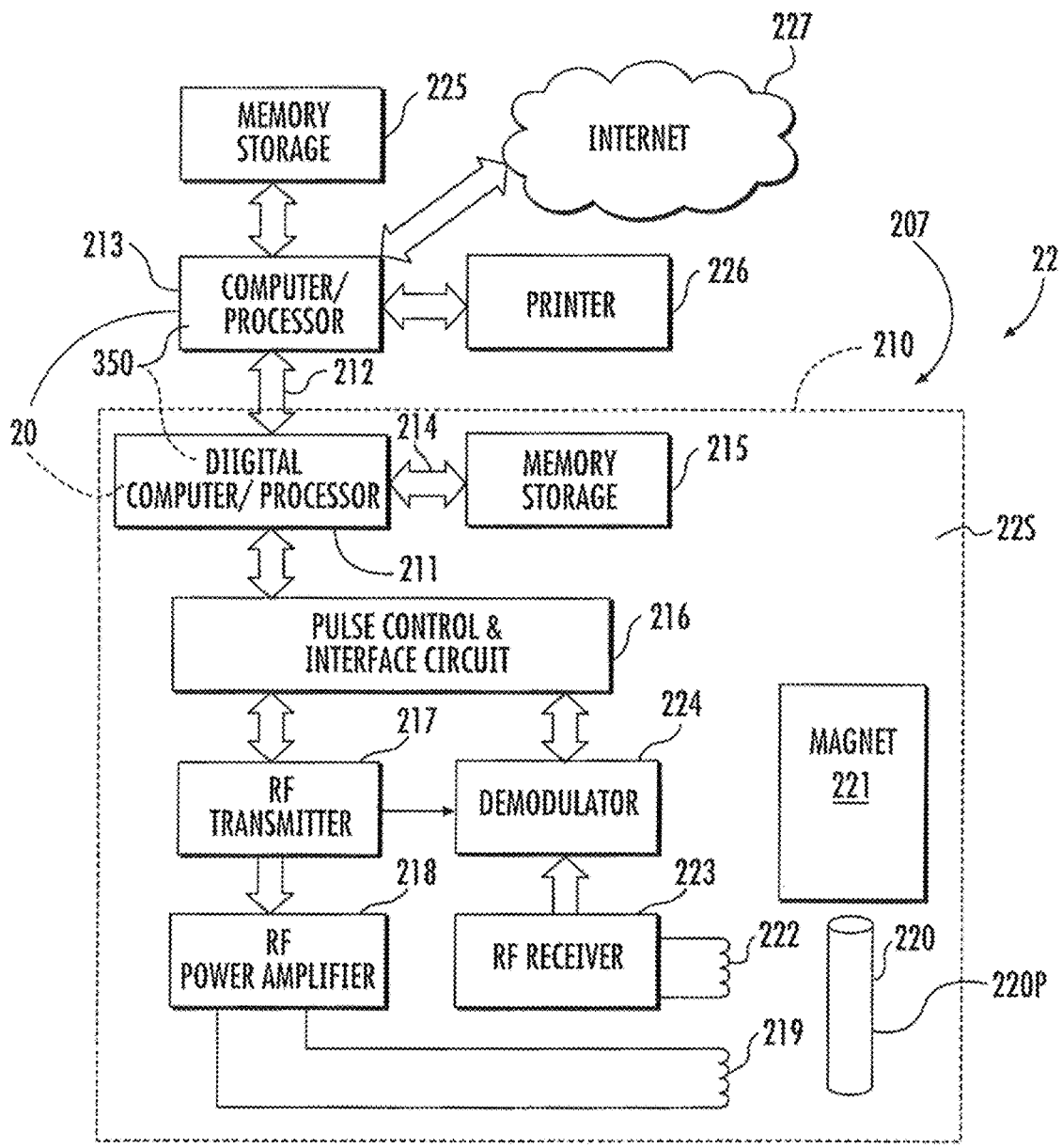
FIG. 7 is a schematic illustration of a NMR spectroscopy apparatus according to embodiments of the present invention.

Referring now to FIG. 7, a system 207 for acquiring and calculating the lineshape of a selected sample is illustrated. The system 207 includes an NMR spectrometer 22s for taking NMR measurements of a sample. In one embodiment, the spectrometer 22s is configured so that the NMR measurements are conducted at 400 MHz for proton signals; in other embodiments the measurements may be carried out at between 200 MHz to about 900 MHz or other suitable frequency. Other frequencies corresponding to a desired operational magnetic field strength may also be employed. Typically, a proton flow probe is installed, as is a temperature controller to maintain the sample temperature at 47+/− 0.5 degrees C. The spectrometer 22s is controlled by a digital computer 211 or other signal processing unit. The computer 211 should be capable of performing rapid Fourier transformations. It may also include a data link 212 to another processor or computer 213, and a direct-memory-access channel 214 which can connects to a hard memory storage unit 215.

The digital computer 211 may also include a set of analog-to-digital converters, digital-to-analog converters and slow device I/O ports which connect through a pulse control and interface circuit 216 to the operating elements of the spectrometer 22s. These elements include an RF transmitter 217 which produces an RF excitation pulse of the duration, frequency and magnitude directed by at least one digital signal processor that can be onboard or in communication with the digital computer 211, and an RF power amplifier 218 which amplifies the pulse and couples it to the RF transmit coil 219 that surrounds sample cell 220 and/or flow probe 220p. The NMR signal produced by the excited sample in the presence of a 9.4 Tesla polarizing magnetic field produced by superconducting magnet 221 is received by a coil 222 and applied to an RF receiver 223. The amplified and filtered NMR signal is demodulated at 224 and the resulting quadrature signals are applied to the interface circuit 216 where they are digitized and input through the digital computer 211. The GlycA measurement and analyzer circuit 20 and/or module 350 (FIGS. 7-8) can be located in one or more processors associated with the digital computer 211 and/or in a secondary computer 213 or other computers that may be on-site or remote, accessible via a worldwide network such as the Internet 227.

After the NMR data are acquired from the sample in the measurement cell 220, processing by the computer 211 produces another file that can, as desired, be stored in the storage 215. This second file is a digital representation of the chemical shift spectrum and it is subsequently read out to the computer 213 for storage in its storage 225 or a database associated with one or more servers. Under the direction of a program stored in its memory or accessible by the computer 213, the computer 213, which may be a laptop computer, desktop computer, workstation computer, electronic notepad, electronic tablet, smartphone or other device with at least one processor or other computer, processes the chemical shift spectrum in accordance with the teachings of the present invention to generate a report which may be output to a printer 226 or electronically stored and relayed to a desired email address or URL. Those skilled in this art will recognize that other output devices, such as a computer display screen, electronic notepad, smartphone and the like, may also be employed for the display of results.

It should be apparent to those skilled in the art that the functions performed by the computer 213 and its separate storage 225 may also be incorporated into the functions performed by the spectrometer's digital computer 211. In such case, the printer 226 may be connected directly to the digital computer 211. Other interfaces and output devices may also be employed, as are well-known to those skilled in this art.

Certain embodiments of the present invention are directed at providing methods, systems and/or computer program products that use GlycA evaluations that may be particularly useful in automated screening tests of clinical disease states and/or risk assessment evaluations for screening of in vitro biosamples.

Embodiments of the present invention may take the form of an entirely software embodiment or an embodiment combining software and hardware aspects, all generally referred to herein as a "circuit" or "module."

As will be appreciated by one of skill in the art, the present invention may be embodied as an apparatus, a method, data or signal processing system, or computer program product. Accordingly, the present invention may take the form of an entirely software embodiment, or an embodiment combining software and hardware aspects. Furthermore, certain embodiments of the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, but is not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium, upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as Java7, Smalltalk, Python, Labview, C++, or VisualBasic. However, the computer program code for carrying out operations of the present invention may also be written in conventional procedural programming languages, such as the "C" programming language or even assembly language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN) or secured area network (SAN), or the connection may be made to an external computer (for example, through the Internet using an Internet Service Provider).

The flowcharts and block diagrams of certain of the figures herein illustrate the architecture, functionality, and operation of possible implementations of analysis models and evaluation systems and/or programs according to the present invention. In this regard, each block in the flow charts or block diagrams represents a module, segment, operation, or portion of code, which comprises one or more executable instructions for implementing the specified logical function(s). It should also be noted that in some alternative implementations, the functions noted in the blocks might occur out of the order noted in the figures. For example, two blocks shown in succession may in fact be executed substantially concurrently or the blocks may sometimes be executed in the reverse order, depending upon the functionality involved.

Figure 8:
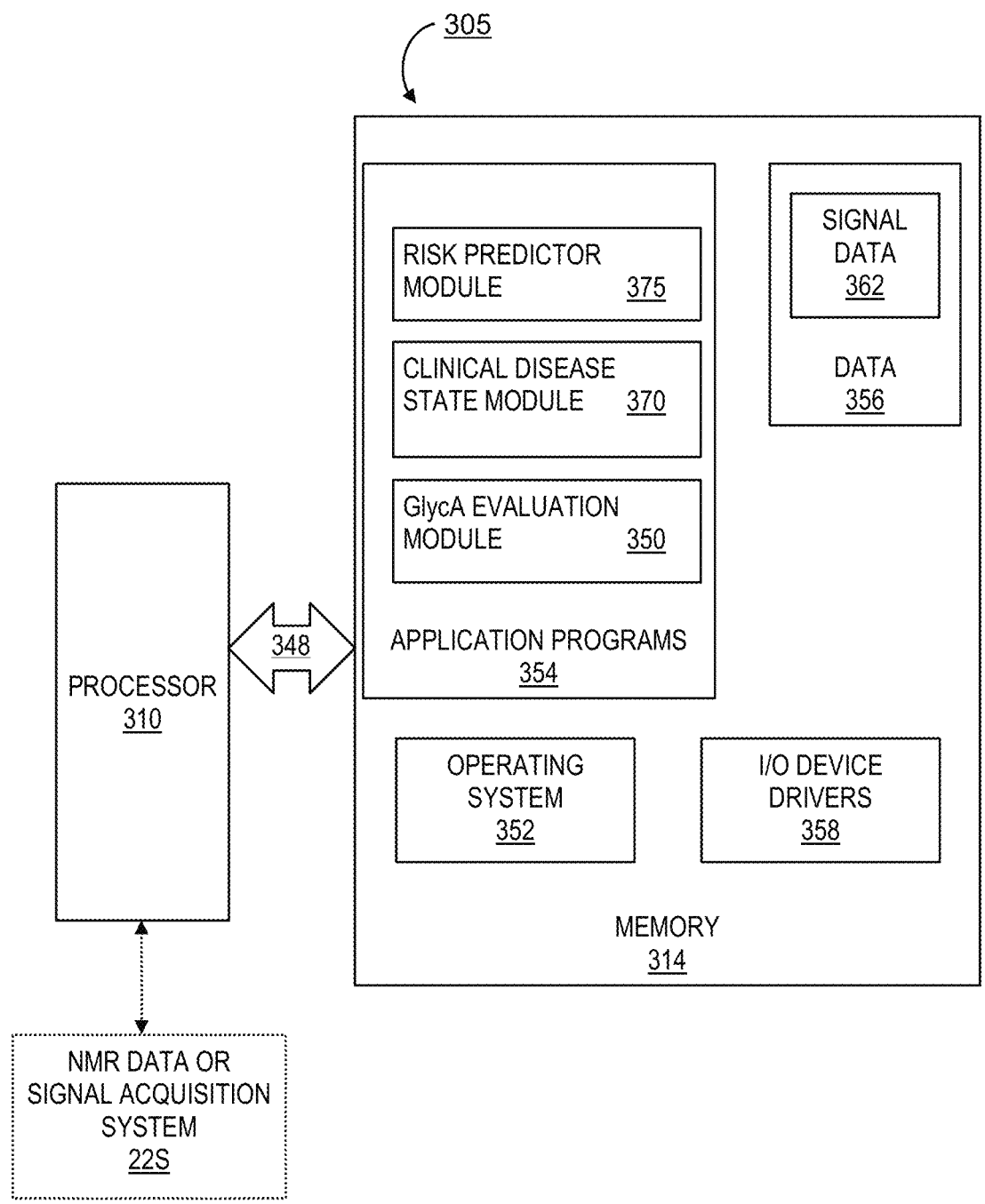
FIG. 8 is a schematic diagram of a data processing system according to embodiments of the present invention.

FIG. 8 is a block diagram of exemplary embodiments of data processing systems 305 that illustrates systems, methods, and computer program products in accordance with embodiments of the present invention. The processor 310 communicates with the memory 314 via an address/data bus 348. The processor 310 can be any commercially available or custom microprocessor. The memory 314 is representative of the overall hierarchy of memory devices containing the software and data used to implement the functionality of the data processing system 305. The memory 314 can include, but is not limited to, the following types of devices: cache, ROM, PROM, EPROM, EEPROM, flash memory, SRAM, and DRAM.

As shown in FIG. 8, the memory 314 may include several categories of software and data used in the data processing system 305: the operating system 352; the application programs 354; the input/output (I/O) device drivers 358; a CRI module 370 and the data 356. The CRC Risk Index Evaluation Module 370 can consider the concentration of the measured GlycA, and optionally also other established CRC risk factors, including but not limited to, BMI, age, alcohol intake, in a multi-parameter mathematical model of risk of developing CRC incidence or mortality in the next 5-7 years.

The data 356 may include signal (constituent and/or composite spectrum lineshape) data 362 which may be obtained from a data or signal acquisition system. As will be appreciated by those of skill in the art, the operating system 352 may be any operating system suitable for use with a data processing system, such as OS/2, AIX or OS/390 from International Business Machines Corporation, Armonk, N.Y., WindowsCE, WindowsNT, Windows95, Windows98, Windows2000 or WindowsXP from Microsoft Corporation, Redmond, Wash., PalmOS from Palm, Inc., MacOS from Apple Computer, UNIX, FreeBSD, or Linux, proprietary operating systems or dedicated operating systems, for example, for embedded data processing systems.

The I/O device drivers 358 typically include software routines accessed through the operating system 352 by the application programs 354 to communicate with devices such as I/O data port(s), data storage 356 and certain memory 314 components and/or the NMR spectrometer or analyzer 22. The application programs 354 are illustrative of the programs that implement the various features of the data processing system 305 and can include at least one application, which supports operations according to embodiments of the present invention. Finally, the data 356 represents the static and dynamic data used by the application programs 354, the operating system 352, the I/O device drivers 358, and other software programs that may reside in the memory 314.

While the present invention is illustrated, for example, with reference to the Modules 350 being an application program in FIG. 8, as will be appreciated by those of skill in the art, other configurations may also be utilized while still benefiting from the teachings of the present invention. For example, the GlycA Module 350 and/or the Clinical Disease State Module 370 may also be incorporated into the operating system 352, the I/O device drivers 358 or other such logical division of the data processing system 305. Thus, the present invention should not be construed as limited to the configuration of FIG. 8, which is intended to encompass any configuration capable of carrying out the operations described herein.

Figure 9:
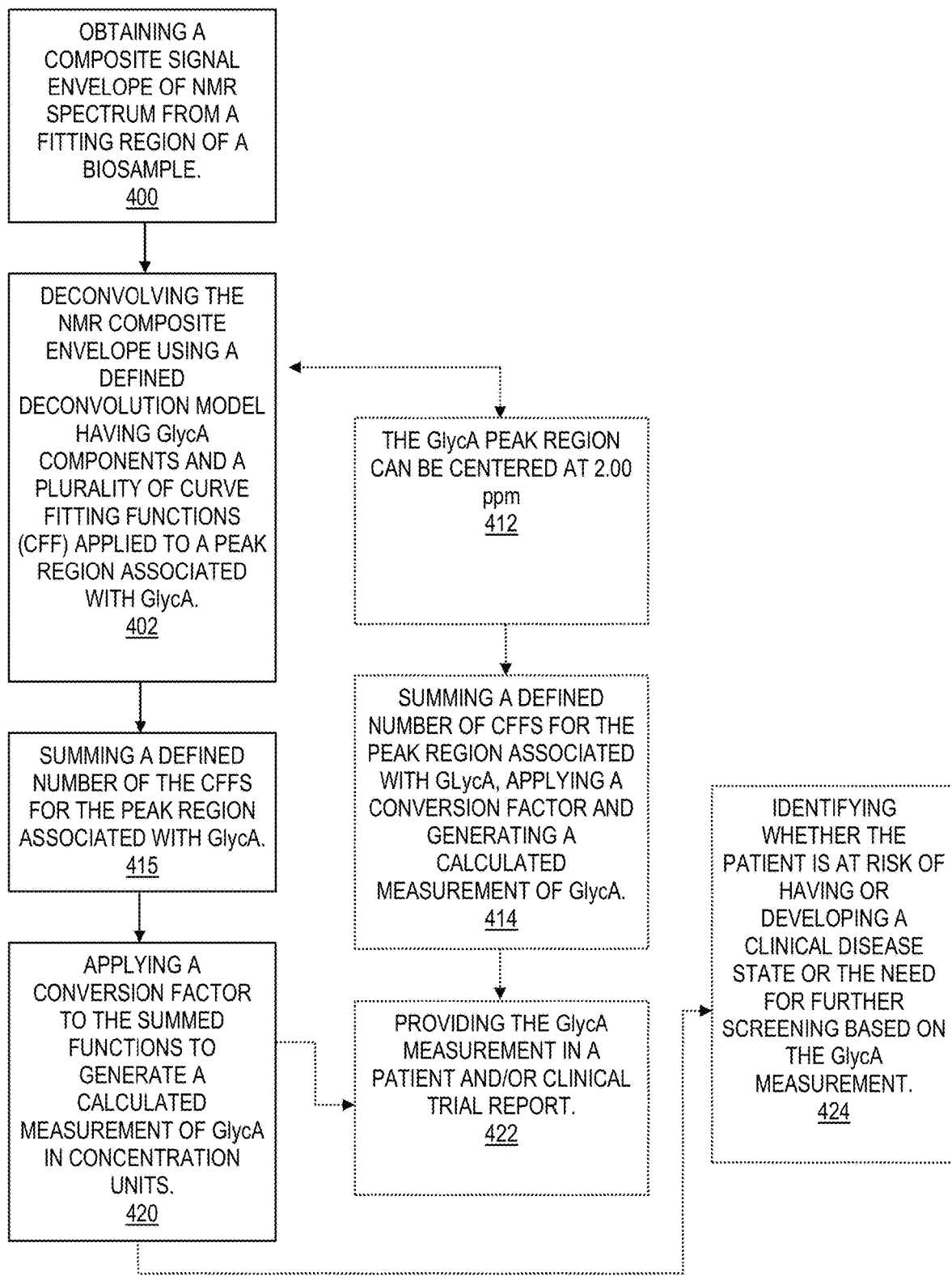
FIG. 9 is a flow chart of exemplary operations that can carry out embodiments of the present invention.

FIG. 9 is a flow chart of exemplary operations that can carry out embodiments of the present invention. As shown, at least one defined mathematical model or risk of CRC incidence or mortality in a future time frame (e.g., in 9, 12, 15, 18, 19, or 20 years) can be provided (block 400). Measurements of components of the at least one mathematical model of a respective patient biosample can be obtained (block 400). A CRI score can be calculated using the model and the measurements (block 414). A patient risk report (paper and/or electronic) with the CRI score can be provided to desired recipients (e.g., a patient and/or clinician) (block 422).

The following paragraphs are non-limiting examples of certain embodiments of the technology:

1. In an embodiment, the disclosure provides a method evaluating a subject's risk of CRC incidence or mortality, the method comprises:
   (a) providing a sample from the subject;
   (b) measuring the GlycA concentration by NMR; and
   (c) determining the risk of CRC incidence or mortality based on the GlycA concentration.

2. The embodiment of paragraph 1, wherein the subject is a healthy subject.

3. The embodiment of any of the above paragraphs, wherein the risk is CRC incidence in the next 5-20 years.

4. The embodiment of paragraph 1, wherein the method is for determining the risk of mortality for a subject having CRC in the next 5-20 years.

5. The embodiment of any of the above paragraphs, wherein the subject is determined to have increased risk of CRC incidence or mortality when the GlycA concentration is in the third or fourth quartile, or a third tertile of a population norm.

6. The embodiment of any of the above paragraphs, wherein the subject is determined to have increased risk of CRC incidence or mortality when the GlycA concentration is at least 370 µmol/L, or at least about 400 µmol/L or at least about 415 µmol/L.

7. In an embodiment, the disclosure provides a method of evaluating the risk of CRC incidence or mortality for a subject, the method comprises:
   (a) providing a sample from the subject;
   (b) measuring the GlycA concentration by NMR and at least one acute phase protein and/or at least one inflammatory protein and/or at least one lipoprotein; and
   (c) determining the subject's risk of CRC incidence or mortality based on the GlycA concentration and the concentration of the at least one acute phase protein and/or at least one inflammatory protein and/or at least one lipoprotein.

8. The embodiment of paragraph 7, wherein the at least one acute phase protein comprises one of fibrinogen, hsCRP or sICAM-1 and/or the at least one lipoprotein comprises ApoA1.

9. The embodiment of paragraphs 7 or 8, wherein the risk is CRC incidence in the next 5-20 years.

10. The embodiment of any one of paragraphs 7-9, wherein the subject is determined to have increased risk of CRC incidence or mortality when the GlycA concentration is in the third or fourth quartile, or a third tertile of a population norm.

11. The embodiment of any one of paragraphs 7-10, wherein the subject is determined to have increased risk of CRC incidence or mortality when the GlycA concentration is at least 370 µmol/L, or at least about 400 µmol/L or at least about 415 µmol/L.

12. In an embodiment, the disclosure provides a method of determining the risk of having increased risk of developing a CRC tumor at a higher Duke stage, a proximal location, or being less differentiated comprises the steps of:
   (a) providing a sample from the subject,
   (b) measuring the GlycA concentration by NMR, and
   (c) determining the subject has increased risk of developing CRC tumor at a higher Duke stage, a proximal location, or being less differentiated for at least one of when the GlycA concentration in the sample is in the third, fourth quartile, or third tertile of a population norm.

13. The embodiment of paragraph 12, wherein the GlycA concentration in the sample is at least 370 µmol/L, or at least about 400 µmol/L or at least about 415 µmol/L.

14. The method of any of the preceding paragraphs, wherein the sample is a whole blood sample, a serum sample, or a plasma sample.

15. In an embodiment, a computer program product for determining the risk of CRC incidence or mortality for a subject comprises:
   computer readable program code for obtaining NMR signal data of a sample of a subject to determine the GlycA concentration in the sample, and computer readable program code for electronically identifying the subject has increased risk of CRC incidence or mortality for at least one of when the GlycA concentration in the sample is third, or fourth quartile of a population norm, or the subject is determined to have increased risk of CRC incidence or mortality when the GlycA concentration is at least 370 µmol/L, or at least about 400 µmol/L or at least about 415 µmol/L.

16. The embodiment of paragraph 15, wherein the risk is CRC incidence in the next 5-20 years.

17. The embodiment of paragraphs 15 or 16, further comprising:
   computer readable program code for obtaining the data of the sample to determine the concentration of at least one acute phase protein and/or at least one inflammatory protein and/or at least one lipoprotein; and
   computer readable program code for electronically determining the risk of CRC incidence or mortality for the subject based on the concentration of GlycA and the concentration of at least one acute phase protein and/or at least one inflammatory protein and/or at least one lipoprotein.

18. The embodiment of paragraph 17, wherein the at least one acute phase protein is at least one of fibrinogen, hsCRP or sICAM and/or the at least one lipoprotein comprises ApoA1.

19. The embodiment of paragraphs 17 or 18, wherein the determining the risk of CRC incidence or morality is based on a CRC risk index comprising the concentration of GlycA and the concentration of the at least one acute phase protein and/or at least one inflammatory protein and/or at least one lipoprotein.

20. In an embodiment, the disclosure provides a computer program product for evaluating whether a treatment is effective in reducing the chance of CRC incidence or mortality for the subject comprises:
   computer readable program code for obtaining NMR signal data of samples taken at two or more time points during the treatment period,
   computer readable program code for determining the GlycA concentration in the samples, and
   computer readable program code for determining the treatment is ineffective if the GlycA concentration increases over time, and determining the treatment is effective if the GlycA concentration decreases over time.

21. The embodiment of paragraph 20, wherein the subject is determined to have increased risk of CRC incidence or mortality when the GlycA concentration is in third or fourth quartile, or third tertile of the population norm, or when the GlycA concentration is at least 370 µmol/L, at least about 400 µmol/L or at least about 415 µmol/L.

22. In an embodiment, the disclosure provides a system for evaluating the risk of CRC incidence or mortality for a subject, comprises:
   an NMR spectrometer for acquiring at least one NMR spectrum of a sample, and a controller in communication with the NMR spectrometer, the controller comprising at least one processor configured to
(i) determine the GlycA concentration from the sample based on the NMR signal data, and
(ii) determine the subject has increased risk of CRC incidence or mortality for at least one of when the GlycA concentration is in third or fourth quartile, or third tertile of the population norm, or when the GlycA concentration is at least, or when the GlycA concentration is at least 370 µmol/L, at least about 400 µmol/L or at least about 415 µmol/L.

23. The embodiment of paragraph 22, wherein the risk is CRC incidence in the next 5-20 years.

24. In an embodiment, the disclosure provides a system for evaluating the risk of CRC incidence or mortality for a subject, comprises:
an NMR spectrometer for acquiring at least one NMR spectrum of a sample, and
a controller in communication with the NMR spectrometer, the controller comprising at least one processor configured to
(i) determine the GlycA concentration in the sample based on the NMR signal data;
(ii) determine the concentration of at least one acute phase protein and/or at least one inflammatory protein and/or at least one lipoprotein in the sample based on the NMR signal data; and
(iii) determine the subject's risk of CRC incidence or mortality based on a CRC risk index comprising the GlycA concentration and the concentration of the at least one acute phase protein and/or at least one inflammatory protein and/or at least one lipoprotein.

25. The embodiment of paragraph 24, wherein the at least one acute phase protein is fibrnogen, hsCRP or sICAM and/or the at least one lipoprotein comprises ApoA1.

26. The embodiment of paragraph 24, wherein the subject is determined to have increased risk of CRC incidence or mortality when the GlycA concentration is in third or fourth quartile, or third tertile of the population norm, or when the GlycA concentration is at least 370 µmol/L, at least about 400 µmol/L, or at least about 415 µmol/L.

27. The embodiment of paragraph 24, wherein the risk is CRC incidence in the next 5-20 years.

EXAMPLES

The following Examples have been included to provide guidance to one of ordinary skill in the art for practicing representative embodiments of the presently disclosed subject matter. In light of the present disclosure and the general concentration of skill in the art, those of skill can appreciate that the following Examples are intended to be exemplary only and that numerous changes, modifications, and alterations can be employed without departing from the scope of the presently disclosed subject matter.

Example 1 WHS and MESA Study Design

The discovery study population was derived from the Women's Health Study (WHS, n=39,876), a completed randomized controlled 2×2×2 factorial trial of aspirin, β-carotene, or vitamin E versus placebo in the primary prevention of cancer and cardiovascular disease. Women were healthcare professionals, ≥45 years old, and free of cancer and cardiovascular disease at study entry (1992-1996). After trial completion, extended post-trial follow-up of participants remained on-going with follow-up reported herein through 2013. Of the 39,876 randomized women in the trial, 28,345 (71%) provided a baseline blood sample. The study was approved by the Human Subjects Committee at the Brigham and Women's Hospital, Boston, Mass.

Figure 5:
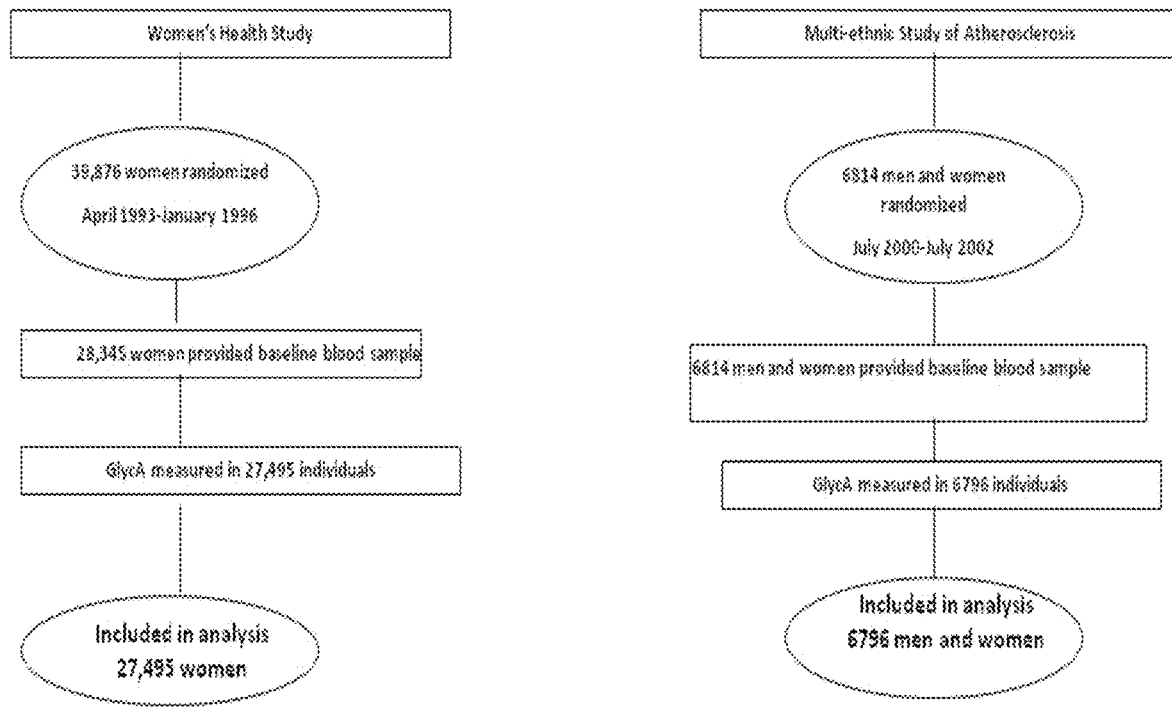
FIG. 5 shows the cohort diagrams for WHS and MESA.

The Multi-Ethnic Study of Atherosclerosis (MESA) is a Replication Cohort which was conducted on multiethnic men and women to evaluate the associations already identified in WHS. Briefly, this community-based study enrolled 6,814 men and women, ages 45-84 years, of African-American (22%), Hispanic (22%), White (28%), and Chinese-American (12%) ethnicity, free of self-reported active treatment of cancer and cardiovascular disease at baseline entry (2000-2002). The study was approved by the institutional review boards of the participating institutions, and subjects gave written informed consent. Standardized questionnaires and procedures were used to determine age, sex, ethnicity, and clinical features. GlycA was measured at baseline among 6,796 of the 6,814 participants. FIG. 5.

Of those alive at the end of trial in 2004 from WHS, 33,682 (85%) consented to continue in the post-trial follow-up of participants. Prior to randomization, blood was requested (but not required) from participants. Women who did and did not donate blood were similar on a wide range of variables related to cancer. Anthropometric, lifestyle, and dietary data were derived from the baseline questionnaire. The validity and reproducibility of the semi-quantitative food-frequency questionnaire (FFQ) and other self-reported variables have been described previously. Written informed consent was obtained from each participant. FIG. 5.

MESA CRC cases (median follow-up 11 years) were identified from hospital records by International Classification of Diseases for Oncology ("ICD")-9 and ICD-10 codes along with National Death Index for CRC deaths. The following ICD codes were used to identify these participants: ICD-9: 153. * (Malignant neoplasm of colon), 154. * (Malignant neoplasm of rectum rectosigmoid junction and anus), ICD-10: C18. * (Malignant neoplasm of colon), C19. * (Malignant neoplasm of rectosigmoid junction), C20. * (Malignant neoplasm of rectum), C21. * (Malignant neoplasm of anus and anal canal). Cancer outcome information was obtained from the records collected during investigation of MESA endpoints of interest (myocardial infarction, angina, congestive heart failure, peripheral vascular disease, stroke, transient ischemic attack, revascularization, and deaths due to cardiovascular disease [CVD]). Only CVD events undergo rigorous physician review for endpoint adjudication. Non-CVD events (such as CRC) do not undergo this physician review and are defined expressly based on the ICD-9/10 codes obtained from discharge summaries (all hospitalizations).

Example 2. Laboratory Measurements

Figure 4:
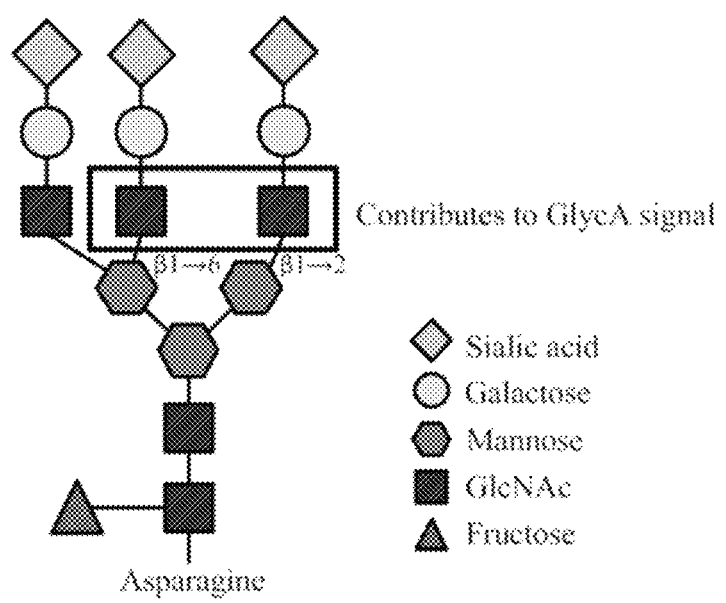
FIG. 4 is the schematic illustration of tri-antennary N-acetyl linked glycan chain, with N-acetylglucosamine (GlcNAc) contributing to the GlycA signal (rectangle box). GlycA identifies bi-, tri-, and tetra-antennary N-linked glycan chains with β1→2 and β1→6 mannose-GlcNAc linkage. Asparagine represents the universal amino acid site for N-glycosylation.

NMR spectroscopy was used to measure circulating plasma GlycA concentration. The plasma 400 Hz $^1$H NMR GlycA signal at 2.00 ppm was quantified using deconvolution software to measure a subset of mobile N-acetylglucosamine (GlcNAc) residues on the bi-, tri-, and tetra-antennary glycan branches of circulating glycoproteins (FIG. 4). Examination of the GlycA spectral region of targeted proteins identified the predominant constituents of GlycA as α1-acid glycoprotein, haptoglobin, α1-antitrypsin, α1-antichymotrypsin, and transferrin. Notably, other acute phase proteins (including fibrinogen, α2-macroglobulin, sICAM-1, and hsCRP) do not contribute to the GlycA signal. GlycA concentration was measured on blood samples obtained at baseline for WHS and MESA that had been collected in EDTA tubes and stored frozen (−170° C. for WHS and −70° C. for MESA). LipoScience (now LabCorp; Raleigh, N.C.) performed the GlycA measurements and reported GlycA intra and inter-assay coefficients of variation as 1.9 and 2.6%, respectively.

In WHS, hsCRP was measured by an immunoturbidimetric assay with reagents and calibrators from Denka Seiken (Tokyo, Japan). sICAM-1 was measured using an enzyme-linked immunosorbent assay (R&D Systems, Minneapolis, Minn.), and fibrinogen was measured using an immunoturbidimetric assay (Kamiya Biomedical, Seattle, Wash.).

Example 3. Ascertainment of CRC Cases and Death

In WHS (median follow-up 19 years), CRC cases were ascertained via annual follow-up questionnaires, letters, and telephone calls. Following written informed consent, medical records were obtained and reviewed by a blinded Endpoints Committee that adjudicated all reported endpoints including CRC based on predefined criteria that are commonly used by medical professionals in pathological evaluations of CRCs. Deaths of participants were identified by reports from family members, postal authorities, and a search of the National Death Index (NDI). Medical records were reviewed to confirm CRC cases. Then the events were coded with ICD codes. Morbidity and mortality follow-up were 97.2 and 99.4% complete, respectively.

Example 4. Models for Statistical Analyses

Relations of GlycA to incident colorectal cancer and mortality were analyzed using multivariable Cox proportional hazards models. In some cases, the multivariable Cox models were adjusted for clinical risk factors (including age, sex, race, family history, body mass index, physical activity, smoking, and alcohol, among others) and compared GlycA risk associations with those of established acute phase proteins (high-sensitivity C-reactive protein, fibrinogen, and soluble intercellular adhesion molecule-1). In WHS, model 1 was adjusted for trial treatment assignments and age ("WHS-model 1"). Model 2 was additionally adjusted for race, family history of CRC, alcohol, exercise, smoking, menopausal status, postmenopausal hormone use (never, past, current); healthy eating index (Alternative Healthy Eating Index, "AHEI"), which is based on foods and nutrients predictive of chronic disease risk), multivitamin use, intake of red meat (servings/day), total vegetable and fruits (servings/day), supplemental and dietary calcium, fiber (grams/day), total calories (kcal/day); history of colonic polyps, body mass index (BMI), and hemoglobin A1C ("WHS-model 2"). The third model included model 2 variables plus one of the markers of systemic inflammation (natural log transformed [ln]hsCRP, fibrinogen, or sICAM-1). In MESA, given the smaller number of events in the replication cohort, risk of CRC incidence and mortality were modeled with two models: model 1 adjusted for age, sex, and race/ethnicity ("MESA-model 1"); model 2 included model 1 variables and adjusted for BMI, exercise (total intentional exercise MET-hrs/wk), smoking, alcohol (drinks/week), and family history of cancer ("MESA-model 2").

Baseline characteristics of participants across quartiles of GlycA were summarized as means (standard deviation [SD]), or medians ($25^{th}$ to $75^{th}$ percentiles) for quantitative variables, and as percentages for qualitative variables. Spearman coefficients were used to correlate GlycA with risk factors and inflammatory biomarkers. Person-years of follow-up and rates were calculated, and cumulative incidence was obtained according to quartiles of GlycA and log-rank test was used to compare curves. Hazard ratios (HRs) and 95% confidence intervals (CIs) of incident CRC events and mortality were calculated from Cox-proportional hazard regression for mid-quartile scores and per SD increment. Exposure time was calculated as the time from enrollment to incidence/death or censoring. For WHS, incident CRC cases only include nonfatal CRC. As there was no significant interaction between CRC, GlycA, and randomization arms (including aspirin), the groups were pooled and indicators of the randomized treatments were included as covariables. SAS version 9.2 (SAS Institute, Cary, N.C., USA) was used for all analyses except the meta-analysis (STATA version 14, College Station, Tex.).

Adjustment for potential confounders or mediators was completed with sequential models. P for trend was calculated across quartiles for WHS and tertiles for MESA (given smaller number of cases, n=70 cases). Although the longitudinal CRC incidence associated with GlycA in WHS did not violate the proportional hazards assumption (p value=0.2 for test of proportional hazard assumption in a model assuming linearity of GlycA), there was a suggestion of a trend graphically. Based on these observations, a stratified incidence analysis was performed to investigate the association between the CRC incidence risks and the GlycA concentrations by follow-up period using the time cutpoints 0-2, 2-5, 5-9, 9-12, 12-15, 15-19 follow-up years. The study also compared the association between CRC cancer incidence and mortality risks and GlycA to that of CRC risks and other established systemic inflammatory biomarkers and (ln hsCRP, fibrinogen, and sICAM-1).

Following replication in MESA, the study specific estimates were combined in a meta-analysis and pooled into Forest plots using random effects models to account for inter-study heterogeneity. For the CRC meta-analysis, WHS incidence cases included fatal and nonfatal cases and MESA incidence cases included fatal and nonfatal cases.

Example 5 Results a. WHS

The mean age (SD) of the WHS cohort at baseline was 54.7 (7.1) years. Stratification by GlycA quartiles identified a higher prevalence of CRC risk factors (e.g. BMI) among those with higher concentrations of GlycA (Table 1). Likewise, concentrations of hsCRP, sICAM-1, and fibrinogen were higher by increasing quartiles of GlycA, and correlated moderately with GlycA with the strongest correlation for hsCRP (Spearman correlation coefficients 0.30 to 0.61; see eTable 1).

TABLE 1

Baseline characteristics of WHS participants by quartiles of GlycA [a]

| | Quartile 1 ≤326 µmol/L | Quartile 2 327-369 µmol/L | Quartile 3 370-416 µmol/L | Quartile 4 >416 µmol/L |
|---|---|---|---|---|
| N | 6992 | 6791 | 6865 | 6847 |
| Age, years | 51 (48, 57) | 53 (49, 59) | 54 (50, 60) | 54 (50, 60) |
| Race/ethnicity, % | | | | |
| Caucasian | 93.7 | 94.8 | 95.1 | 94.5 |
| Hispanic | 1.0 | 1.2 | 1.1 | 1.0 |
| Black | 1.7 | 1.7 | 1.6 | 2.4 |
| Asian/Pacific Islander | 2.5 | 1.3 | 1.1 | 0.6 |
| American Indian/Alaskan Native | 0.3 | 0.3 | 0.5 | 0.5 |
| Postmenopausal, % | 45.9 | 53.8 | 57.5 | 60.5 |
| Randomized aspirin, % [b] | 50.3 | 48.3 | 50.7 | 50.7 |
| Randomized vitamin E, % [c] | 49.9 | 51.1 | 49.3 | 49.9 |
| Randomized beta carotene, % [c] | 49.6 | 50.0 | 49.3 | 50.3 |
| Body mass index, kg/m² mean (SD) | 23.6 (3.5) | 25.1 (4.2) | 26.5 (4.7) | 28.7 (5.7) |
| Physical activity, MET-hrs/week, mean (SD) | 17.8 (20.8) | 15.9 (19.5) | 13.5 (16.7) | 11.7 (15.5) |
| Smoking, % | | | | |
| Current | 7.7 | 10.6 | 12.6 | 15.8 |
| Past | 36.7 | 37.6 | 36.9 | 35.4 |
| Never | 55.6 | 51.8 | 50.3 | 48.7 |
| Family history of CRC, % [c] | 10.0 | 10.7 | 10.6 | 10.3 |
| History of polyps, % [d] | 2.1 | 2.7 | 2.7 | 2.7 |
| Fruit and vegetable intake, servings/d, mean (SD) [d] | 6.2 (3.9) | 6.2 (3.5) | 6.1 (3.4) | 6.0 (3.6) |
| Fiber intake, g/d, mean (SD) | 19.4 (8.4) | 19.1 (8.0) | 19.1 (8.3) | 18.7 (8.0) |
| Red meat, servings/d, mean (SD) | 0.7 (0.5) | 0.7 (0.6) | 0.7 (0.6) | 0.8 (0.6) |
| Dietary calcium, mg/d, mean (SD) [b] | 794.1 (357.0) | 789.7 (357.7) | 792.6 (359.8) | 775.9 (355.2) |
| Alcohol, g/d, mean (SD) | 4.7 (8.1) | 4.5 (8.6) | 4.0 (8.2) | 3.3 (8.0) |
| Total calories, kcal/d, mean (SD) [c] | 1718 (515.5) | 1726 (524.0) | 1737 (531) | 1738 (545) |
| Multivitamin use, % [c] | 86.2 | 85.4 | 86.3 | 85.2 |
| Lipid lowering medications, % | 1.2 | 2.3 | 3.2 | 6.0 |
| Postmenopausal hormone use-current, % | 35.5 | 40.8 | 45.3 | 49.0 |
| Diabetes, % | 1.0 | 1.5 | 2.1 | 4.9 |
| Hemoglobin A1c, % | 4.9 (4.8, 5.1) | 5.0 (4.8, 5.2) | 5.0 (4.9, 5.2) | 5.1 (4.9, 5.3) |
| hsCRP, mg/L | 0.7 (0.4, 1.5) | 1.5 (0.7, 2.9) | 2.6 (1.4, 4.6) | 5.1 (2.8, 8.3) |
| sICAM, ng/mL | 317 (281, 360) | 337 (297, 383) | 349 (308, 400) | 373 (328, 430) |
| Fibrinogen, mg/dL | 314 (279, 350) | 341 (304, 384) | 363 (321, 409) | 402 (353, 457) |

Data presented as median (25th percentile, 75th percentile) unless otherwise indicated.
Abbreviations:
BMI = body mass index,
MET-hrs/wk = metabolic equivalent hours per week,
hsCRP = high sensitivity C-reactive protein,
sICAM-1 = soluble intracellular adhesion molecule 1
[a] P value < 0.0001 unless otherwise indicated.
[b] P value = 0.01
[c] P value > 0.05
[d] 0.01 < P value < 0.05 eTABLE 1

Spearman correlation coefficients (r) between GlycA
and acute phase reactants in WHS and MESA*
GlycA, μmol/L

| | WHS | | MESA | |
|---|---|---|---|---|
| | r | N | r | N |
| Fibrinogen | 0.46 | 27,308 | 0.47 | 6,753 |
| hsCRP | 0.61 | 27,458 | 0.55 | 6,750 |
| ICAM-1 | 0.30 | 27,297 | 0.20 | 2,617 |

Abbreviations: hsCRP = high-sensitivity C-reactive protein, ICAM-1 = soluble intracellular adhesion molecule 1, WHS = Women's Health Study, MESA = Multi-Ethnic Study of Atherosclerosis, N = number of individuals, and r = correlation.
*All correlations p < 0.0001.

Incident CRC and Mortality:

Over a median follow-up of 19 years among the 27,495 WHS participants (FIG. 5), 337 incident CRC cases and 103 CRC deaths occurred. For WHS, incident CRC cases only include nonfatal CRC. Cumulative incidence curves for CRC events (adjusted for age) diverged according to quartiles of GlycA (FIG. 1A, p for log-rank<0.0001; Table 2). The risk factor-adjusted WHS-model 2 analysis showed that the HR [95% CI] per SD (68.4 μmol/L) higher GlycA for CRC incidence was 1.19 [1.06-1.35], p=0.004, and the HR per SD higher GlycA for CRC mortality was 1.24 [1.00-1.55], p=0.05 (Table 2). The results showed CRC incidence and mortality increased by quartiles of GlycA with minimal attenuation after adjustment for clinical variables in model 2, i.e., body mass index ("BMI"), etc.

TABLE 2

Colorectal cancer incidence and mortality by quartiles of baseline GlycA in the Women's Health Study*

| | Quartile 1 | Quartile 2 | Quartile 3 | Quartile 4 | P for trend | Per SD* | P Value |
|---|---|---|---|---|---|---|---|
| Range, μmol/L | ≤326 | 327-369 | 370-416 | >416 | | | |
| Incident CRC, N cases/total | 61/6992 | 70/6791 | 86/6865 | 120/6847 | | | |
| Incident Rate per 1,000 person-years | 0.52 | 0.62 | 0.76 | 1.09 | | | |
| CRC deaths, N cases/total | 19/6992 | 21/6791 | 26/6865 | 37/6847 | | | |
| Death Rate per 1,000 person-years | 0.15 | 0.17 | 0.21 | 0.31 | | | |
| Incident CRC, model 1 | 1.0 (ref) | 1.08 (0.77-1.53) | 1.29 (0.93-1.79) | 1.83 (1.35-2.50) | <0.0001 | 1.26 (1.13-1.39) | <0.0001 |
| Incident CRC, model 2 | 1.0 (ref) | 1.05 (0.73-1.51) | 1.23 (0.87-1.75) | 1.55 (1.09-2.20) | 0.006 | 1.19 (1.06-1.35) | 0.004 |
| CRC death, model 1 | 1.0 (ref) | 1.01 (0.54-1.88) | 1.21 (0.67-2.19) | 1.74 (1.00-3.03) | 0.02 | 1.29 (1.07-1.55) | 0.008 |
| CRC death, model 2 | 1.0 (ref) | 0.92 (0.47-1.80) | 1.26 (0.67-2.36) | 1.46 (0.77-2.76) | 0.15 | 1.24 (1.00-1.55) | 0.05 |

*Model 1 Hazard ratio from Cox regression models adjusted for age and trial treatment assignment Model 2 Hazard ratio from Cox regression models adjusted for age, trial treatment assignment, race, family history of colorectal cancer, alcohol, exercise, smoking, menopausal status, postmenopausal hormone use; alternative healthy eating index, multivitamin use; intake of red meat, vegetables and fruits, supplemental and dietary calcium, fiber, total calories, history of polyps, body mass index, and hemoglobin A1c.

SD represents standard deviation (68 μmol/L) for baseline GlycA in WHS.

Evidence of GlycA-CRC Risk Beyond the Other Acute Phase Proteins

Examination of hsCRP, sICAM-1, and fibrinogen with CRC risk factor-adjusted model 2 per SD yielded no significant associations with CRC incidence or mortality with any of the systemic inflammatory biomarkers with the exception of fibrinogen (see eTable 2 in Supplement). Fibrinogen was significantly associated with increased risk of CRC death in quartile analysis Q1 to Q4, 1.0 (ref), 0.97 [0.4502.11], 1.79 [0.90-3.57], 1.81 [0.90-3.66], p for trend=0.04, but the association was not significant for per 1 SD increment of fibrinogen, p=0.33.

ETABLE 2

WHS colorectal cancer incidence and mortality by quartiles of baseline GlycA, hsCRP, sICAM-1, and fibrinogen

|  | Q1 | Q2 | Q3 | Q4 | P-linear trend | 1-SD | P-value |
|---|---|---|---|---|---|---|---|
| GlycA | | | | | | | |
| Range, μmol/L | ≤326 | 327-369 | 370-416 | >416 | P for trend | Per SD* | P Value |
| Incident CRC, model 1 | 1.0 (ref) | 1.08 (0.77-1.53) | 1.29 (0.93-1.79) | 1.83 (1.35-2.50) | <0.0001 | 1.27 (1.14-1.41) | <0.0001 |
| Incident CRC, model 2 | 1.0 (ref) | 1.05 (0.74-1.51) | 1.24 (0.89-1.77) | 1.55 (1.09-2.20) | 0.006 | 1.19 (1.06-1.35) | 0.004 |
| CRC death, model 1 | 1.0 (ref) | 1.01 (0.54-1.88) | 1.21 (0.67-2.19) | 1.74 (1.00-3.03) | 0.02 | 1.33 (1.10-1.61) | 0.003 |
| CRC death, model 2 | 1.0 (ref) | 0.92 (0.47-2.80) | 1.26 (0.67-2.37) | 1.46 (0.77-2.77) | 0.14 | 1.24 (1.00-1.54) | 0.05 |
| Fibrinogen | | | | | | | |
| Range, mg/dL | ≤308 | >308-351 | >351-403 | >403 | | | |
| Incident CRC, Model 1 | 1.0 (ref) | 1.05 (0.74-1.49) | 1.17 (0.83-1.64) | 1.59 (1.16-2.20) | 0.001 | 1.11 (0.99-1.24) | 0.08 |
| Incident CRC, Model 2 | 1.0 (ref) | 1.01 (0.71-1.44) | 1.04 (0.73-1.48) | 1.31 (0.92-1.85) | 0.09 | 1.01 (0.90-1.14) | 0.89 |
| CRC death, Model 1 | 1.0 (ref) | 1.12 (0.52-2.39) | 2.12 (1.09-4.13) | 2.39 (1.24-4.61) | 0.002 | 1.26 (1.03-1.55) | 0.02 |
| CRC death, Model 2 | 1.0 (ref) | 0.97 (0.45-2.11) | 1.79 (0.90-3.57) | 1.81 (0.90-3.67) | 0.04 | 1.12 (0.89-1.41) | 0.33 |
| HsCRP | | | | | | | |
| Range, mg/L | ≤0.8 | >0.8-2 | >2-4.4 | >4.4 | | | |
| Incident CRC, Model 1 | 1.0 (ref) | 0.85 (0.61-1.18) | 0.99 (0.72-1.36) | 1.16 (0.85-1.57) | 0.11 | 1.09 (0.98-1.23) | 0.13 |
| Incident CRC, Model 2 | 1.0 (ref) | 0.79 (0.56-1.11) | 0.84 (0.60-1.18) | 0.88 (0.61-1.26) | 0.93 | 0.99 (0.86-1.14) | 0.91 |
| CRC death, Model 1 | 1.0 (ref) | 1.02 (0.55-1.91) | 1.30 (0.72-2.35) | 1.30 (0.72-2.35) | 0.33 | 1.11 (0.90-1.38) | 0.32 |
| CRC death, Model 2 | 1.0 (ref) | 1.00 (0.53-1.89) | 1.13 (0.60-2.15) | 1.08 (0.54-2.16) | 0.82 | 1.02 (0.79-1.31) | 0.90 |
| sICAM-1 | | | | | | | |
| Range, ng/mL | 74-301 | >301-343 | >343-395 | >395 | | | |
| Incident CRC, Model 1 | 1.0 (ref) | 1.07 (0.76-1.51) | 1.24 (90.89-1.72) | 1.40 (1.02-1.94) | 0.02 | 1.10 (0.98-1.23) | 0.12 |
| Incident CRC, Model 2 | 1.0 (ref) | 1.04 (0.73-1.47) | 1.13 (0.80-1.58) | 1.16 (0.82-1.65) | 0.35 | 1.01 (0.89-1.15) | 0.84 |
| CRC death, Model 1 | 1.0 (ref) | 0.99 (0.53-1.83) | 0.88 (0.47-1.65) | 1.48 (0.84-2.60) | 0.11 | 1.20 (0.98-1.47) | 0.08 |

ETABLE 2-continued

WHS colorectal cancer incidence and mortality by quartiles of baseline GlycA, hsCRP, sICAM-1, and fibrinogen

|  | Q1 | Q2 | Q3 | Q4 | P-linear trend | 1-SD | P-value |
|---|---|---|---|---|---|---|---|
| CRC death, Model 2 | 1.0 (ref) | 0.93 (0.50-1.73) | 0.79 (0.42-1.49) | 0.99 (0.53-1.84) | 0.99 | 1.02 (0.81-1.28) | 0.89 |

\* Model 1: Hazard ratio from Cox regression models adjusted for age and trial treatment assignment
Model 2: Hazard ratio from Cox regression models adjusted for age, trial treatment assignment, race, family history of colorectal cancer, alcohol, exercise, smoking, menopausal status, postmenopausal hormone use; alternative healthy eating index, multivitamin use; intake of red meat, vegetables and fruits, supplemental and dietary calcium, fiber, total calories, history of polyps, body mass index, and hemoglobin A1c.
SD represents standard deviation for baseline inflammatory biomarkers in WHS (1.20 mg/L for hsCRP, 0.22 ng/mL for sICAM-1, 0.22 mg/dL for fibrinogen); hsCRP, fibrinogen, and sICAM-1 were log transformed.
Abbreviations: hsCRP = high sensitivity C-reactive protein, sICAM-1 = soluble intracellular adhesion molecule 1

Sensitivity analyses were performed to investigate the potential risk associated with GlycA beyond the known markers of systemic inflammation (eTable 3). Incident CRC risk associated with GlycA remained significant after additionally adjusting for any of the three systemic inflammatory biomarkers (hsCRP, fibrinogen, or sICAM-1). For example, the GlycA risk for CRC incidence and mortality remained significant after incrementally adjusting for hsCRP, HR [95% CI] was 1.27 [1.10-1.45] for incident CRC and 1.31 [1.01-1.68] for mortality. In models that included both fibrinogen and GlycA, the association between GlycA and CRC became slightly stronger for incident CRC after adjusting for fibrinogen, HR [95% CI] per 1 SD GlycA was 1.19 (p=0.004) without fibrinogen and 1.22 (p=0.03) with fibrinogen. For CRC death, the addition of fibrinogen to model 2 had minimal impact on the association between GlycA and CRC death.

Stratification by CRC Risk Factors:

In WHS analyses stratified by CRC risk factors such as age, BMI, aspirin or NSAID use, increasing GlycA remained associated with increased risk of incident CRC with no evidence of effect modification by the established CRC risk factors (p for interaction≥0.06 for all subgroups except multivitamin subgroup p for interaction=0.05) (FIG. 2A). The WHS data were stratified by CRC risk factors and multivariate hazard ratios (HRs) for incident colorectal cancer were adjusted for trial treatment assignment, age, race, family history of colorectal cancer, alcohol, exercise, smoking, post-menopausal versus premenopausal, post-menopausal hormone use-never, past, current; alternative healthy eating index continuous, multivitamin yes/no current use; red meat intake servings/d, total vegetable and fruits intake servings/day, supplemental calcium, dietary calcium, fiber grams/day, total calories, history of polyps,

ETABLE 3

Association of GlycA with incident colorectal cancer and colorectal cancer death after additionally adjusting for inflammatory biomarkers
Quartiles of Baseline GlycA

|  | Q1 | Q2 | Q3 | Q4 | P linear trend | 1-SD | P value |
|---|---|---|---|---|---|---|---|
| GlycA | | | | | | | |
| Range, umol/L | ≤326 | 327-369 | 370-416 | ≥416 | | | |
| CRC Incidence | | | | | | | |
| Model 2 | 1.0 (ref) | 1.05 (0.73-1.50) | 1.23 (0.87-1.75) | 1.55 (1.09-2.20) | 0.006 | 1.19 (1.06-1.35) | 0.004 |
| Model 2 + fibrinogen | 1.0 (ref) | 1.07 (0.74-1.53) | 1.26 (0.88-1.79) | 1.62 (1.12-2.35) | 0.005 | 1.22 (1.07-1.39) | 0.003 |
| Model 2 + hsCRP | 1.0 (ref) | 1.09 (0.76-1.57) | 1.33 (0.93-1.92) | 1.76 (1.20-2.60) | 0.002 | 1.27 (1.10-1.45) | 0.0009 |
| Model 2 + sICAM-1 | 1.0 (ref) | 1.05 (0.73-1.51) | 1.24 (0.87-1.75) | 1.56 (1.09-2.23) | 0.006 | 1.20 (1.06-1.35) | 0.004 |
| CRC Death | | | | | | | |
| Model 2 | 1.0 (ref) | 0.92 (0.47-1.80) | 1.26 (0.67-2.36) | 1.46 (0.77-2.76) | 0.14 | 1.24 (1.00-1.54) | 0.05 |
| Model 2 + fibrinogen | 1.0 (ref) | 0.90 (0.46-1.77) | 1.21 (0.64-2.30) | 1.38 (0.70-2.71) | 0.24 | 1.23 (0.97-1.56) | 0.09 |
| Model 2 + hsCRP | 1.0 (ref) | 0.95 (0.48-1.86) | 1.33 (0.69-2.56) | 1.54 (0.76-3.14) | 0.15 | 1.31 (1.01-1.68) | 0.04 |
| Model 2+ sICAM-1 | 1.0 (ref) | 0.92 (0.47-1.80) | 1.26 (0.67-2.36) | 1.47 (0.77-2.79) | 0.15 | 1.25 (1.00-1.56) | 0.049 |

Model 2: Hazard ratio from Cox regression models adjusted for, age, trial treatment assignment, race, family history of colorectal cancer, aspirin use (current use >once/week versus none), alcohol, exercise, smoking, menopausal status, postmenopausal hormone use; alternative healthy eating index, multivitamin use; intake of red meat, vegetables and fruits, supplemental and dietary calcium, fiber, total calories, history of polyps, body mass index, and hemoglobin A1c.
SD represents standard deviation for baseline GlycA in WHS (68 μmol/L for GlycA); hsCRP, fibrinogen, and sICAM-1 were log transformed.
Abbreviations: hsCRP = high sensitivity C-reactive protein, sICAM-1 = soluble intracellular adhesion molecule 1 randomized aspirin use during trial period, randomized vitamin E use during trial period, entire follow-up period for aspirin arm, entire follow-up period for vitamin E arm.

Sensitivity Analysis by Follow-Up Time eTable 4 shows the HR [95% CI] per SD by follow-up year interval. Additionally, WHS sensitivity analysis that excluded the first 2 years of follow-up in order to examine potential reverse causation between GlycA and CRC, model 2 HR [95% CI] per SD higher GlycA was 1.10 [0.95-1.28]; p=0.22. Excluding the first 5 years of follow-up, HR [95% CI] per SD was 1.27 [1.12-1.43], p=0.0002. The observed point-estimates were also similar for the association between GlycA and incident CRC and mortality during the aspirin and vitamin E trial 10-year treatment period (208 CRC cases and 51 deaths, data not shown). Similar results were seen with a model adjusted for age, race, treatment randomization, family history of colorectal cancer, aspirin use, current use of asa>1×/wk versus no aspirin, alcohol, exercise, smoking, post menopausal versus premenopausal, postmenopausal hormone use-never, past, current; healthy eating index continuous, multivitamin yes/no current use; red meat intake servings/d, total vegetable and fruits intake servings/day, supplemental calcium, dietary calcium, fiber grams/day, total calories continuous, history of polyps, A1C.

eTABLE 4

Baseline GlycA and incident colorectal cancer in WHS by follow-up years

| Follow-up years | No. cases/Total N | HR* per SD | 95% CI | P value |
|---|---|---|---|---|
| 0 to 2 | 28/27,495 | 1.29 | (0.83-1.99) | 0.26 |
| 2 to 5 | 62/27,096 | 1.12 | (0.85-1.49) | 0.42 |
| 5 to 9 | 85/26,346 | 1.05 | (0.82-1.34) | 0.72 |
| 9 to 12 | 73/24,925 | 1.26 | (0.97-1.64) | 0.08 |
| 12 to 15 | 47/22,045 | 1.21 | (0.87-1.67) | 0.26 |
| 15 to 19 | 40/20,740 | 1.56 | (1.12-2.17) | 0.009 |

*Hazard ratio from Cox regression models adjusted for age, trial treatment assignment, race, family history of colorectal cancer, alcohol, exercise, smoking, menopausal status, postmenopausal hormone use; alternative healthy eating index, multivitamin use; intake of red meat, vegetables and fruits, supplemental and dietary calcium, fiber, total calories, history of polyps, body mass index, and hemoglobin A1c.
SD represents standard deviation (68 μmol/L) for baseline GlycA in WHS.

Associations with Tumor Characteristics

In WHS exploratory analyses, some CRC tumor characteristics were significantly associated with GlycA (FIG. 2B), including higher Duke stage, proximal tumor location, and less differentiated tumors. The hazard ratios shown in FIG. 2B were adjusted for age, trial treatment assignment, race, family history of colorectal cancer, alcohol, exercise, smoking, post-menopausal versus premenopausal, postmenopausal hormone use-never, past, current; alternative healthy eating index continuous, multivitamin yes/no current use; red meat intake servings/d, total vegetable and fruits intake servings/day, supplemental calcium, dietary calcium, fiber grams/day, total calories, history of polyps, body mass index, hemoglobin A1c. Horizontal lines represent 95% confidence intervals per GlycA SD.

b. MESA Replication:

Among 6,784 MESA participants (median follow-up: 11 years) 70 incident CRC cases and 23 CRC deaths occurred (FIG. 1B). For MESA, incident CRC cases included fatal CRC. Compared with WHS, MESA participants were older (mean [SD] age of 62.2 [10.2]) and were 47.2% male (see eTable 5 in Supplement). CRC incidence and mortality in MESA were increased per SD (62 μmol/L) increment in GlycA in all models (see eTable 6 in Supplement). Age-, sex- and race-adjusted model 1 HRs (95% CIs) per SD for incident CRC and mortality were, respectively, 1.32 (1.06-1.65), p=0.01, and 1.54 (1.06-2.23), p=0.02. This risk resembled the observed association in WHS, and the effect estimate was consistent with WHS but was no longer statistically significant in model 2.

eTABLE 5

Baseline clinical and biochemical variables by GlycA tertile in MESA[a]

| | Tertiles of GlycA, umol/L | | |
|---|---|---|---|
| | <351 (n = 2265) | 351-404 (n = 2285) | ≥405 (n=)2234 |
| Incident colorectal cancer cases | 18 | 19 | 33 |
| GlycA, mean (SD), μmol/L | 317.3 (25.4) | 377.2 (15.1) | 451.5 (42.1) |
| Age, years, mean (SD)[b] | 61.7 (10.4) | 62.6 (10.2) | 62.2 (10.1) |
| Women, % | 39.5 | 52.3 | 66.8 |
| Race/ethnicity, (%) | | | |
| Caucasian | 37.3 | 40.2 | 38.1 |
| Black | 25.7 | 26.3 | 31.0 |
| Chinese | 18.1 | 11.7 | 5.7 |
| Hispanic | 18.9 | 21.8 | 25.3 |
| Body mass index (kg/m²) | 26.7 (4.7) | 28.2 (5.2) | 30.1 (6.0) |
| Physical activity (MET-hr/wk) | 29.7 (39.9) | 25.5 (41.4) | 22.5 (35.1) |
| hsCRP, mg/L | 1.6 (2.0) | 3.1 (3.9) | 6.8 (8.4) |
| Smoking status, (%) | | | |
| Current | 24.29.4 | 31.312.1 | 44.517.6 |
| Past | 35.238.7 | 3336.7 | 31.134.7 |
| Never | 34.552.0 | 34.351.2 | 31.347.8 |
| Alcohol (no. drinks/week)[c] | 4.3 (8.8) | 3.8 (7.7) | 4.0 (9.1) |
| Family history of cancer, %[c] | 54.4 | 56.7 | 57.8 |

Abbreviations: BMI = body mass index, hsCRP = high sensitivity C-reactive protein, MET-hrs/wk = metabolic equivalent hours per week. Data presented as mean (standard deviation) otherwise as percent where indicated.
[a]P value < 0.001 unless otherwise indicated.
[b]P value = 0.009
[c]P value > 0.05

ETABLE 6

MESA colorectal cancer incidence and mortality by tertiles of GlycA*

| | Q1 | Q2 | Q3 | P Linear trend | Per 1 SD* | P Value |
|---|---|---|---|---|---|---|
| | ≤351 | 351-404 | ≥404 | | | |
| Incident CRC, N cases/total | 18/2265 | 19/2285 | 33/2234 | | | |
| Incident Rate per 1,000 person-years | 0.76 | 0.80 | 1.48 | | | |
| CRC deaths, N cases/total | 4/2265 | 6/2285 | 13/2234 | | | |

ETABLE 6-continued

MESA colorectal cancer incidence and mortality by tertiles of GlycA*

|  | Q1 | Q2 | Q3 | P Linear trend | Per 1 SD* | P Value |
|---|---|---|---|---|---|---|
| Death Rate per 1,000 person-years | 0.17 | 0.25 | 0.58 |  |  |  |
| Incident CRC, Model 1 | 1.0 (ref) | 0.99 (0.52-1.91) | 1.87 (1.03-3.40) | 0.02 | 1.32 (1.06-1.65) | 0.01 |
| Incident CRC, Model 2 | 1.0 (ref) | 0.98 (0.50-1.91) | 1.57 (0.83-2.97) | 0.12 | 1.21 (0.95-1.55) | 0.12 |
| CRC death, Model 1 | 1.0 (ref) | 1.18 (0.33-4.25) | 2.63 (0.83-8.39) | 0.06 | 1.54 (1.06-2.23) | 0.02 |
| CRC death, Model 2 | 1.0 (ref) | 1.39 (0.44-5.66) | 2.41 (0.64-9.14) | 0.14 | 1.34 (0.88-2.03) | 0.17 |

Abbreviations: BMI = body mass index, MET-hrs/wk = metabolic equivalent hours per week. Model 1: adjusted for age, race, gender. Model 2: Model 1 + BMI, exercise (total intentional exercise MET-hr/wk), smoking, alcohol (number drinks per week), family history of cancer.
SD represents standard deviation (62 μmol/L for GlycA)

c. Combination Analysis

Figure 3A:
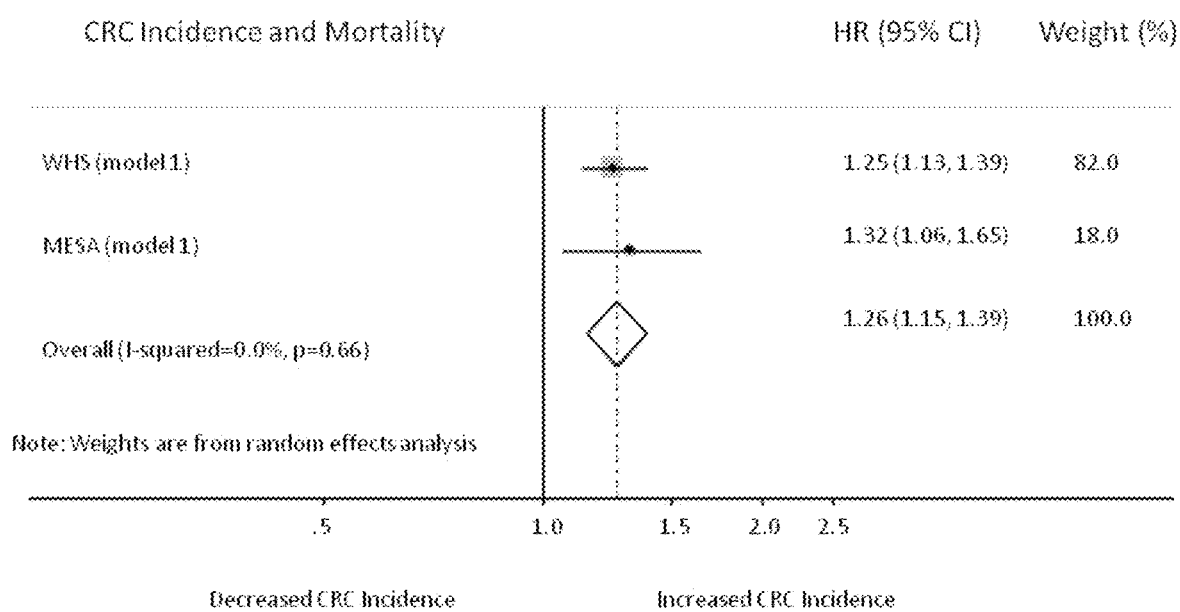
FIG. 3A-3B show forest plots that demonstrate the individual and pooled associations (using hazard ratio and 95% confidence interval) between GlycA and colorectal cancer incidence and mortality in Women's Health Study (WHS) and Multi-Ethnic Study of Atherosclerosis (MESA). The association between GlycA and CRC incidence and mortality is shown in FIG. 3A (model 1 analysis) and FIG. 3B (model 2 analysis).
Figure 3B:
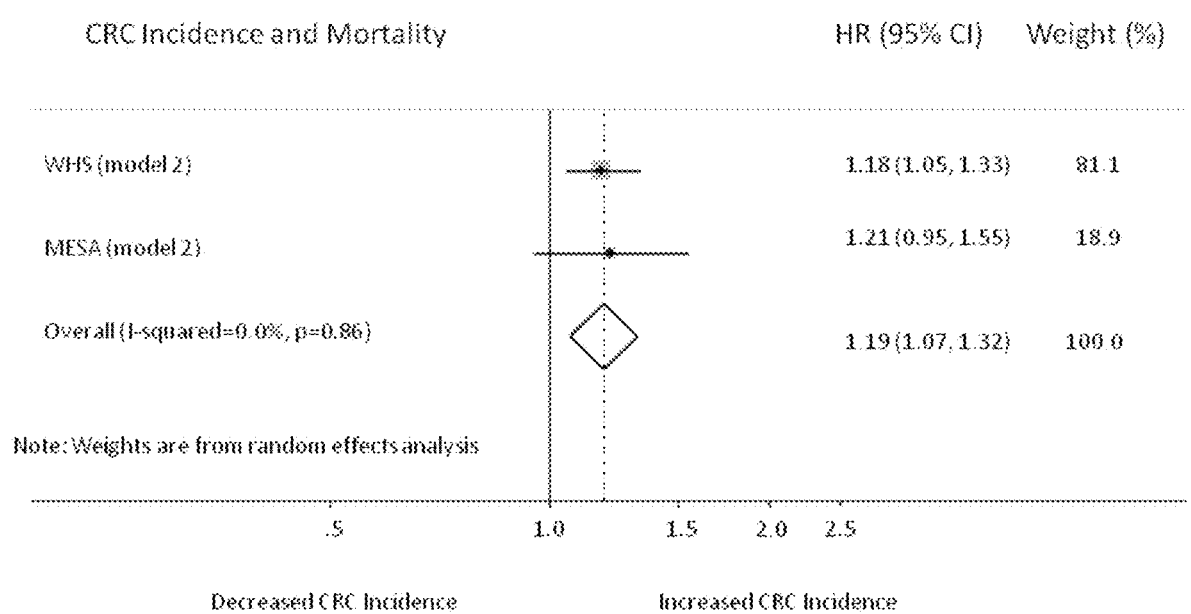

From random effects meta-analysis of the CRC incidence and mortality in both WHS and MESA cohorts per SD increment in GlycA, the pooled model 1 HR (95% CI) per SD for CRC incidence was 1.26 [1.15-1.39], p=1×10$^{-6}$ with no significant heterogeneity (I-squared=0% p=0.66), with similar results for the more fully adjusted model 2 (FIGS. 3A-3B). FIG. 3A-3D show forest plots that demonstrate the individual and pooled associations (hazard ratio [95% confidence interval]) between GlycA and cancer incidence and mortality in Women's Health Study (WHS) and Multi-Ethnic Study of Atherosclerosis (MESA).

What is claimed is:

1. A method of measuring GlycA concentration, the method comprising:
   (a) providing a sample from a subject with colorectal cancer; and,
   (b) using NMR, determining if the GlycA concentration in the sample is at least 370 μmol/L.

2. The method of claim 1, wherein the subject is not showing symptoms associated with the colorectal cancer.

3. The method of claim 1, wherein step (b) further comprises, using the NMR, determining if the GlycA concentration in the sample is in a third quartile, a fourth quartile, or a third tertile of a population norm.

4. The method of claim 1, wherein step (b) comprises, using the NMR, determining if the GlycA concentration in the sample is at least about 400 μmol/L or at least 415 μmol/L.

5. A method of measuring GlycA concentration, the method comprising:
   providing a sample from a subject with colorectal cancer;
   measuring by NMR if the GlycA concentration in the sample is at least 370 μmol/L; and,
   measuring concentration in the sample of at least one acute phase protein and/or at least one inflammatory protein and/or at least one lipoprotein.

6. The method of claim 5, wherein the at least one acute phase protein comprises one of fibrinogen, hsCRP or sICAM-1 and/or the at least one lipoprotein comprises ApoA1.

7. The method of claim 5, wherein the measuring by the NMR further comprises determining if the GlycA concentration in the sample is in a third quartile, a fourth quartile, or a third tertile of a population norm.

8. The method of claim 5, wherein the measuring by the NMR comprises measuring if the GlycA concentration in the sample is at least about 400 μmol/L or at least about 415 μmon.

9. A method of measuring GlycA concentration comprising:
   (a) providing a sample from a subject with colorectal cancer, and
   (b) measuring by NMR if the GlycA concentration in the sample is at least 370 μmol/L and is in a third quartile, a fourth quartile, or a third tertile of a population norm.

10. The method of claim 9, wherein step (b) comprises measuring by the NMR if the GlycA concentration in the sample is at least about 400 μmol/L or at least about 415 μmol/L.

11. The method of claim 1, wherein the sample is a whole blood sample, a serum sample, or a plasma sample.

12. A method for measuring GlycA change during a colorectal cancer ("CRC") treatment for a drug-treated subject with colorectal cancer, comprising:
   (a) obtaining a first sample and a second sample from the drug-treated subject with colorectal cancer, wherein the first sample and the second sample are obtained at a first time point and a second time point during a treatment period; and
   (b) measuring GlycA concentration in each of the first sample and the second sample by NMR.

13. The method of claim 12, wherein the first sample and the second sample is a whole blood sample, a serum sample, or a plasma sample.

14. The method of claim 5, wherein the sample is a whole blood sample, a serum sample, or a plasma sample.

15. The method of claim 9, wherein the sample is a whole blood sample, a serum sample, or a plasma sample.

16. The method of claim 5, wherein the wherein the subject is not showing symptoms associated with the colorectal cancer.

17. The method of claim 9, wherein the subject is not showing symptoms associated with the colorectal cancer.

* * * * *

UNITED STATES PATENT AND TRADEMARK OFFICE
CERTIFICATE OF CORRECTION

| | | |
|---|---|---|
| PATENT NO. | : 11,124,837 B2 | Page 1 of 1 |
| APPLICATION NO. | : 15/612719 | |
| DATED | : September 21, 2021 | |
| INVENTOR(S) | : James D. Otvos, Samia Mora and Paulette Denise Chandler | |

It is certified that error appears in the above-identified patent and that said Letters Patent is hereby corrected as shown below:

On the Title Page

At item (72) Inventors:
Delete "Sarnia Mora" and insert --Samia Mora--

Signed and Sealed this
Eighteenth Day of November, 2025

John A. Squires
*Director of the United States Patent and Trademark Office*